(12) United States Patent
Brouillette et al.

(10) Patent No.: US 11,065,645 B2
(45) Date of Patent: *Jul. 20, 2021

(54) METHOD AND SYSTEM FOR GENERATING MECHANICAL PULSES

(71) Applicant: Les Solutions Medicales Soundbite Inc., Saint-Laurent (CA)

(72) Inventors: Martin Brouillette, Sherbrooke (CA); Steven Dion, Sherbrooke (CA); Louis-Philippe Riel, Montreal (CA)

(73) Assignee: Les Solutions Medicales Soundbite Inc., Saint-Laurent (CA)

( * ) Notice: Subject to any disclaimer, the term of this patent is extended or adjusted under 35 U.S.C. 154(b) by 236 days.

This patent is subject to a terminal disclaimer.

(21) Appl. No.: 15/568,684

(22) PCT Filed: Apr. 25, 2016

(86) PCT No.: PCT/IB2016/052339
§ 371 (c)(1),
(2) Date: Oct. 23, 2017

(87) PCT Pub. No.: WO2016/170520
PCT Pub. Date: Oct. 27, 2016

(65) Prior Publication Data
US 2018/0147606 A1    May 31, 2018

Related U.S. Application Data

(60) Provisional application No. 62/152,332, filed on Apr. 24, 2015.

(51) Int. Cl.
*B06B 3/00* (2006.01)
*B06B 1/06* (2006.01)
(Continued)

(52) U.S. Cl.
CPC .......... *B06B 3/00* (2013.01); *A61B 17/22004* (2013.01); *A61B 17/22012* (2013.01);
(Continued)

(58) Field of Classification Search
CPC ........ A61B 17/22004; A61B 17/22012; A61B 2017/00477; A61B 2017/22008;
(Continued)

(56) References Cited

U.S. PATENT DOCUMENTS 5,289,436 A    2/1994  Terhune
5,400,788 A    3/1995  Dias et al.
(Continued)

FOREIGN PATENT DOCUMENTS

EP    0386479 A2    9/1990
FR    3006448 A1    12/2014
(Continued)

OTHER PUBLICATIONS

Montaldo et al. "Generation of very high pressure pulses with 1-bit time reversal in a solid waveguide". J. Acoust. Soc. Am. 110 (6), Dec. 2001. (Year: 2001).*

(Continued)

*Primary Examiner* — Michael T Rozanski
(74) *Attorney, Agent, or Firm* — Taft Stettinius & Hollister LLP

(57) ABSTRACT

A method for generating a mechanical wave, including generating a high amplitude mechanical pulse; coupling the mechanical pulse in a proximal end of a transmission member; propagating the mechanical pulse into the transmission member from the proximal end and a distal end thereof; and transmitting the mechanical pulse at the distal end.

24 Claims, 8 Drawing Sheets

(51) Int. Cl.
*A61B 17/22* (2006.01)
*G10K 11/24* (2006.01)
*G10K 11/28* (2006.01)
*B06B 1/02* (2006.01)
*G10K 15/04* (2006.01)
*A61B 17/00* (2006.01)

(52) U.S. Cl.
CPC .......... *B06B 1/0215* (2013.01); *B06B 1/0607* (2013.01); *B06B 1/0633* (2013.01); *G10K 11/24* (2013.01); *G10K 11/28* (2013.01); *G10K 15/043* (2013.01); *A61B 2017/00477* (2013.01); *A61B 2017/22008* (2013.01); *A61B 2017/22018* (2013.01); *A61B 2017/22024* (2013.01); *A61B 2017/22027* (2013.01); *A61B 2017/22028* (2013.01); *B06B 2201/76* (2013.01)

(58) Field of Classification Search
CPC .......... A61B 2017/22018; A61B 2017/22024; A61B 2017/22027; A61B 2017/22028; B06B 1/0215; B06B 1/0607; B06B 1/0633; B06B 2201/76; B06B 3/00; G10K 11/24; G10K 11/28; G10K 15/043
See application file for complete search history.

(56) References Cited

U.S. PATENT DOCUMENTS

| | | | |
|---|---|---|---|
| 5,940,347 | A | 8/1999 | Raida et al. |
| 6,047,602 | A | 4/2000 | Lynnworth |
| 6,343,511 | B1 | 2/2002 | Lynnworth et al. |
| 6,400,648 | B1 | 6/2002 | Heijnsdijk et al. |
| 6,912,918 | B1 | 7/2005 | Lynnworth et al. |
| 8,037,766 | B2 | 10/2011 | Bercoff et al. |
| 2006/0029525 | A1 | 2/2006 | Laugharn, Jr. et al. |
| 2010/0058869 | A1 | 3/2010 | Cawley et al. |
| 2012/0194303 | A1 | 8/2012 | Pettus et al. |
| 2013/0158453 | A1 | 6/2013 | Brouillette et al. |
| 2014/0065575 | A1 | 3/2014 | Altshuler et al. |
| 2014/0202249 | A1 | 7/2014 | Luo et al. |

FOREIGN PATENT DOCUMENTS

| | | |
|---|---|---|
| SU | 1630854 A1 | 2/1991 |
| WO | 1992022259 A2 | 12/1992 |
| WO | 2012025833 A2 | 3/2012 |
| WO | 2016170520 A1 | 10/2016 |

OTHER PUBLICATIONS

International Search Report; Canadian Intellectual Property Office; International Application No. PCT/IB2016/052339; dated Jul. 27, 2016; 6 pages.

Written Opinion of the International Searching Authority; Canadian Intellectual Property Office; International Application No. PCT/IB2016/052339 dated Jul. 27, 2016; 17 pages.

Interindustry Internet-based system for searching and synthesizing the physical principles of operation of energy converters; General Effects Catalog—Scientific and technical effects (STE); http://www.heuristic.su/effects/catalog/tech/byld/description/525/index.html; 2 pages.

* cited by examiner

METHOD AND SYSTEM FOR GENERATING MECHANICAL PULSES

CROSS REFERENCE TO RELATED APPLICATIONS

This application is a U.S. National Phase of International PCT Application No. PCT/IB2016/052339 filed on Apr. 25, 2016, which claims the benefit of U.S. Provisional Application No. 62/152,332 filed Apr. 24, 2015, the contents of each application hereby incorporated by reference in their entirety.

TECHNICAL FIELD

The present invention relates to the field of methods and systems for generating mechanical pulses.

BACKGROUND

Cardiovascular disease remains a leading cause of death worldwide. Atherosclerosis consists of plaque accumulation along the inner wall of arteries. Chronic total occlusion (CTO) represents the complete blockage of a blood vessel. These occlusions are difficult to recanalize using traditional percutaneous transluminal angioplasty (PTA) techniques and apparatus. Procedural success is defined as the ability to pass a standard PTA device across the CTO. PTA procedural shortcomings and complications are usually higher for CTOs. The presence of calcifications and fibrotic tissues within CTO lesions together with the vessel size and tortuosity may be the cause of the potential complications. Therefore, a significant amount of CTOs are treated using an invasive bypass surgery. However, there are benefits of crossing CTOs using PTA procedures. Moreover, some experts believe that new devices and technologies in the field of PTA may improve the success rate and reduce the procedure time for CTO interventions.

Over the years, various apparatus and methods have been developed and proposed to achieve CTO recanalization through minimally invasive procedure. For example, devices have used a mechanical impactor with or without the use of a transmission member, a narrowband ultrasonic source with a transmission wire, and various other methods of energy deposition near the CTO lesion.

For procedures performed using a mechanical impactor, a projectile is accelerated and impacts a proximal end of a transmission member or a distal cap that is in direct contact with the occlusion. The projectile can be accelerated using a pneumatic source, a solenoid, a mechanical spring or other means. The mass of the projectile and its speed at impact produce high stresses at the impact surface and therefore require commensurate maintenance. Also, this method may offer very limited control over the parameters of the mechanical pulse that is generated. Moreover, such devices may be noisy.

Another prior art example consists in a system comprising an ultrasonic wire excited at resonance with a horn and a stacked transducer. This constitutes a first example associated with the use of a narrowband source. This arrangement is used to amplify the displacement at the distal end of the device in contact with the occlusion. The ultrasonic wire is usually used inside a dedicated catheter with cooling fluid circulation. By doing so, the device becomes bulkier and thus is limited in its ability to reach CTOs in small and tortuous anatomy. Considerable loss (due to signal distortion and nonlinearity) and/or mode conversion (from axial to transverse) may also occur at a bend when the device is activated. The frequency of operation (typically around 20 kHz) may create large stress, strain and heat conversion at the ultrasonic wire junction with the horn and within the ultrasonic wire itself. This may contribute to weaken the ultrasonic wire resulting in higher risk of failure.

A second example of a narrowband source is associated with the use of multiple resonant elements distributed in a phased array manner to generate and transmit ultrasonic energy along a transmission line. For example, all resonant elements transmit ultrasonic energy perpendicular to the axis of the waveguide (i.e. radial waves). As a result, most of the energy may be trapped inside the proximal end member, thus making the device inefficient. In another example, shear waves resonant elements are used to induce longitudinal propagating waves inside the waveguide wire (i.e. axial waves). The bond joint between these shear wave resonant elements and the waveguide may be an issue, as the bonding medium (e.g. epoxy) may fail rapidly and/or may add significant attenuation due to bonding material absorption. Therefore, such apparatuses may be limited in terms of power and robustness.

Other prior art forms of energy deposition can be used near the CTO lesion. For example, electromechanical transducer(s) can be used at or near the distal end of a catheter to produce mechanical waves near the occlusion. Such a method may be limited in terms of the power that can be generated considering its miniature size. Moreover, the fabrication of this transducer may be complex and expensive especially considering that the device must be discarded after utilization to prevent contamination. Also, electrical wires are needed to drive the transducer(s) which can leak current inside the body and impact normal heart rhythm.

Laser energy may be used with optical fibers to effectively deliver pulses of high intensity light at the occlusion lesion. However, the inherent fragility of optical fibers makes them prone to break, especially when used in tortuous anatomy. Moreover, this form of energy may be difficult to control and thus be unsafe to nearby healthy tissues; this also necessitates costly laser sources.

Radiofrequency (RF) energy is another prior art source of energy that can be delivered at the occlusion site using electrodes and high voltage (i.e. 1 kV or higher). However, RF energy may be limited in terms of control capability and may tend to create large heat deposition resulting in damage to nearby healthy tissues. Electrical spark discharge can also be used to generate Shockwaves near the occlusion, which requires even higher voltages (i.e. greater than 2 kV). For certain designs, erosion and mechanical wear of the electrodes may represent safety and reliability issues. Furthermore, for safety issues, devices using electrical discharges in the heart need to be synchronized with the patient's heart rhythm, which must thus be predictable and constant.

Chemical detonations can also be used to accelerate a distal hard mass causing it to impact a nearby occlusion. Chemical reactions may be difficult to control and contain, especially in in-vivo environments. Toxic and potentially hazardous products can also be associated with detonations and explosions.

Therefore, it appears that impactors, narrowband energy sources and other prior art methods of energy deposition near vascular occlusions all present drawbacks.

Therefore, there is a need for an improved method and system for generating mechanical waves to treat occlusions for example.

SUMMARY

In accordance with a first broad aspect, there is provided a method for generating a mechanical wave, comprising:

generating at least one high amplitude mechanical pulse; coupling the at least one mechanical pulse into a proximal end of a transmission member; propagating the at least one mechanical pulse into the transmission member from the proximal end to a distal end thereof; and transmitting the at least one mechanical pulse at the distal end of the transmission member.

In one embodiment, the step of generating comprises generating a plurality of mechanical waves having a first amplitude and combining the mechanical waves, thereby obtaining at least one high amplitude mechanical pulse each having a second amplitude greater than the first amplitude.

In one embodiment, the step of combining comprises focusing the mechanical waves on a focus zone.

In one embodiment, the step of focusing comprising reflecting the mechanical waves on a parabolic surface.

In another embodiment, the step of combining comprising propagating the mechanical waves into a temporal concentrator.

In a further embodiment, the step of combining comprises propagating the mechanical waves in a taper.

In still another embodiment, the step of combining comprises propagating the mechanical waves in a reverberating cavity In still a further embodiment, the step of combining comprises propagating the mechanical waves in a dispersive medium.

In one embodiment, the at least one high amplitude mechanical pulse each have a center frequency fc comprised between about 20 kHz and about 10 MHz and a duration of about 1/fc.

In one embodiment, an amplitude of the at least one high amplitude mechanical pulse when reaching the distal end of the transmission member is comprised between about 10 MPa and about 1000 MPa.

In accordance with a second broad aspect, there is provided a system for generating a mechanical wave, comprising: a pulse generator for generating at least one high amplitude and short duration mechanical pulse; and a transmission member extending between a proximal end and a distal end, the proximal end being coupled to the pulse generator for receiving the at least one mechanical pulse therefrom, the transmission member for propagating the at least one mechanical pulse from the proximal end to the distal end and transmitting the at least one mechanical pulse at the distal end.

In one embodiment, the pulse generator comprises: a plurality of broadband sources each for emitting a respective mechanical wave having a first amplitude; and a wave concentrator for combining the mechanical waves in order to obtain the mechanical pulse having a second amplitude greater than the first amplitude.

In one embodiment, the wave concentrator is a spatial concentrator.

In another embodiment, the wave concentrator is a temporal concentrator.

In one embodiment, the wave concentrator is adapted to focus the mechanical waves on a focus zone adjacent to the proximal end of the transmission member.

In one embodiment, the wave concentrator comprises a parabolic reflecting surface for reflecting at least some of the mechanical waves generated by the broadband sources towards the focus zone.

In another embodiment, the wave concentrator is a taper.

In a further embodiment, the wave concentrator comprises a spatial concentration stage and a temporal concentration stage.

In one embodiment, the at least one high amplitude mechanical pulse each have a center frequency $f_c$ comprised between about 20 kHz and about 10 MHz and a duration of about $1/f_c$.

In one embodiment, an amplitude of the at least one high amplitude mechanical pulse when reaching the distal end of the transmission member is comprised between about 10 MPa and about 1000 MPa.

According to a third broad aspect, there is provided a concentrator for focusing mechanical waves emitted by mechanical wave sources, comprising: a body extending between a transmission face comprising a focal zone thereon and a reflection face opposite to the transmission face, the transmission face for receiving at least one mechanical wave source and transmitting at least one mechanical wave emitted by the at least one mechanical wave source within the body, the reflection face being unparallel to the transmission face so as to reflect the at least one mechanical wave emitted by the at least one mechanical wave source towards the focal zone of the transmission face in order to focus the at least one mechanical wave and propagate the at least one focused mechanical wave into a transmission member positioned at the focal zone, and the focusing of the at least one mechanical wave resulting in a greater amplitude mechanical wave having an amplitude being greater than an amplitude of the at least one mechanical wave emitted by the at least one mechanical wave source.

In one embodiment, the focal zone is located substantially at a center of the transmission face.

In one embodiment, the reflection face comprises at least one sloped section each facing a respective one of the at least one mechanical wave source when received on the transmission face and each oriented so as to reflect the at least one mechanical wave emitted by the at least one mechanical wave source towards the focal zone.

In one embodiment, the reflection face has a substantially parabolic shape adapted to reflect the at least one mechanical wave emitted by the at least one mechanical wave source towards the focal zone.

In one embodiment, the reflection face has a truncated parabolic shape, the reflection face having a source receiving section thereon for receiving a further mechanical source for emitting a further mechanical wave to be combined at the focal zone with the at least one mechanical wave emitted by the at least one mechanical wave source.

In one embodiment, the source receiving section substantially faces the focal zone of the transmission face.

In one embodiment, the source receiving section is substantially planar.

In one embodiment, the transmission face is substantially planar.

In one embodiment, the concentrator further comprises at least one protrusion extending from the transmission face, the at least one protrusion defining at least one recess each for receiving a respective one of the at least one mechanical wave source therein.

In one embodiment, the transmission face comprises at least one rounded section each for receiving a respective one of the at least one mechanical wave source having a rounded emission end.

In one embodiment, a section of the transmission face containing the focal zone is substantially planar for coupling the greater amplitude mechanical wave into a waveguide having a substantially planar end.

In one embodiment, a section of the transmission face containing the focal zone is rounded for coupling the greater amplitude mechanical wave into a waveguide having a rounded end.

In one embodiment, the transmission face is adapted to receive at least two concentric sources of mechanical waves.

In one embodiment, the at least one mechanical wave source comprises at least one of an annular mechanical wave source and a hexagonal annular mechanical wave source.

In accordance with a fourth broad aspect, there is provided a connection device for connecting together two mechanical waveguides, comprising: a female connector defining a first aperture for receiving a first mechanical waveguide therein, the first mechanical waveguide comprising a first flange adjacent a first end thereof, an internal face of the female connector comprising a protrusion; a male connector defining a second aperture for receiving a second mechanical waveguide therein, the second mechanical waveguide comprising a second flange adjacent a second end thereof, the male connector having a connection end insertable into the first aperture of the female connector; a first bushing insertable around the first mechanical waveguide, the first bushing comprising a first abutment face for abutment against the first flange of the first mechanical waveguide and a second abutment face for abutment against the protrusion located on the internal face of the female connector; and a second bushing insertable around the second mechanical waveguide and comprising a third abutment face for abutment against the second flange of the second mechanical waveguide and a fourth abutment face for abutment against the connection end of the male connector.

In one embodiment, the connection end of the male connector comprises a beveled recess and the fourth abutment face of the second bushing is beveled for abutment on the beveled recess of the male connector.

In one embodiment, the protrusion of the female connector is beveled and the second abutment face of the first bushing is beveled for abutment against the beveled protrusion.

In one embodiment, the male connector comprises a tubular section adjacent to the connection end and the first aperture of the female connector comprises a cylindrical section, the tubular section of the male connector being insertable into the cylindrical section of the first aperture of the female connector.

In one embodiment, the tubular section of the male connector comprises a first thread extending on an external surface thereof and an internal face of the female connector comprises a second thread extending in the cylindrical section of the first aperture, the second thread matching the first thread so that the male and female connectors be threadingly securable together.

In one embodiment, the first and second bushings are made of plastic first material being different from a second material, the male and female connectors being made of the second material.

In one embodiment, the first and second bushings are made of plastic.

In one embodiment, the first bushing is adapted to abut against the first flange that extends around a whole circumference of the first mechanical waveguide and the second bushing is adapted to abut against the second flange that extends around a whole circumference of the second mechanical waveguide.

In one embodiment, one of the first and second mechanical waveguides comprises a tapering section.

In accordance with another broad aspect, there is provided a connection device for connecting together two mechanical waveguides, comprising: a male connector defining a first aperture for receiving a first mechanical waveguide therein, the first mechanical waveguide comprising a first flange adjacent a first end thereof, the first aperture comprising a first section for receiving the first flange of the first mechanical waveguide and a second section, an internal face of the male connector comprising a first protrusion defining the second section of the first aperture, the first protrusion comprising a first abutment face for abutment against the first flange of the first mechanical waveguide, and dimensions of the second section of the first aperture being greater than dimensions of the first mechanical waveguide so that the first protrusion is not in physical contact with the first mechanical waveguide when the first mechanical waveguide is inserted into the male connector; and a female connector defining a second aperture for receiving a second mechanical waveguide therein, the second mechanical waveguide comprising a second flange adjacent a second end thereof, the second aperture comprising a third section for receiving therein the second flange of the second mechanical waveguide and a portion of the male connector, and a fourth section, an internal face of the female connector comprising a second protrusion defining the fourth section of the second aperture, the second protrusion comprising a second abutment face for abutment against the second flange of the second mechanical waveguide, and dimensions of the fourth section of the second aperture being greater than dimensions of the second mechanical waveguide so that the second protrusion is not in physical contact with the second mechanical waveguide when the second mechanical waveguide is inserted into the female connector.

In one embodiment, the first and second apertures are cylindrical, the second section of the first aperture having a diameter being greater than a diameter of the first mechanical waveguide and being less than a diameter of the first flange, and the fourth section of the second aperture having a diameter being greater than a diameter of the second mechanical waveguide and being less than a diameter of the second flange.

In one embodiment, the portion of the male connector insertable into the female connector comprises a first thread extending on an external surface thereof, and an internal surface of the female connector comprising a second thread within the third section of the second aperture, and the second thread matching the first thread so that the male and female connectors be threadingly securable together.

In one embodiment, the first protrusion is adapted to abut against the first flange that extends around a whole circumference of the first mechanical waveguide and the second protrusion is adapted to abut against the second flange that extends around a whole circumference of the second mechanical waveguide.

In one embodiment, one of the first and second mechanical waveguides comprises a tapering section.

In accordance with a further broad aspect, there is provided a connection device for connecting together two mechanical waveguides, comprising: a male connector defining a first aperture for receiving a first mechanical waveguide therein, an internal surface of the male connector comprising a plurality of teeth projecting therefrom; and a female connector defining a second aperture for receiving a second mechanical waveguide therein, the second mechanical waveguide comprising a flange adjacent an end thereof, an internal face of the female connector comprising a protrusion for abutment against the flange of the second mechanical waveguide, and the second aperture being adapted to receive at least a portion of the male connector therein.

In one embodiment, the male connector comprises a tubular body extending along a longitudinal axis and having an opening extending along the longitudinal axis for allowing an insertion of the first mechanical waveguide therein.

In one embodiment, the male connector comprises a first thread extending along portion of the male connector insertable into the female connector, and an internal face of the female connector comprises a second thread, the second thread matching the first thread so that the male and female connectors be threadingly securable together.

In one embodiment, the male connector comprises two hemi-tubular bodies, wherein the teeth each project from an internal face of a respective one of the two hemi-tubular bodies.

In one embodiment, each one of the two hemi-tubular bodies comprises a first thread on an external face thereof and an internal face of the female connector comprises a second thread, the second thread matching the first thread so that the male and female connectors be threadingly securable together.

In one embodiment, the connection device further comprises securing means for securing the two hemi-tubular bodies together around the first mechanical waveguide.

In one embodiment, the teeth are pointed.

In one embodiment, the teeth have a pyramidal shape.

In another embodiment, the teeth have a conical shape.

In one embodiment, the teeth are each adapted to be received in a respective groove located on a lateral face of the first mechanical waveguide.

In accordance with a further broad aspect, there is provided a connection device for connecting together two mechanical waveguides, comprising: a male connector defining a first aperture for receiving a first mechanical waveguide therein, the first mechanical waveguide comprising a plurality of teeth projecting from a lateral face thereof; and a female connector defining a second aperture for receiving a second mechanical waveguide therein, the second mechanical waveguide comprising a flange adjacent an end thereof, an internal face of the female connector comprising a protrusion for abutment against the flange of the second mechanical waveguide, and the second aperture being adapted to receive at least a portion of the male connector therein.

In one embodiment, the male connector comprises a tubular body extending along a longitudinal axis and having an opening extending along the longitudinal axis for allowing an insertion of the first mechanical waveguide therein.

In one embodiment, the male connector comprises a first thread extending along portion of the male connector insertable into the female connector, and an internal face of the female connector comprises a second thread, the second thread matching the first thread so that the male and female connectors be threadingly securable together.

In one embodiment, an internal face of the tubular body comprises grooves each for receiving a respective of the teeth.

In one embodiment, the grooves are pointed.

In one embodiment, the grooves each have a pyramidal shape.

In another embodiment, the grooves each have a conical shape.

In another embodiment, the male connector comprises two hemi-tubular bodies, wherein the teeth each project from an internal face of a respective one of the two hemi-tubular bodies.

In one embodiment, each one of the two hemi-tubular bodies comprises a first thread on an external face thereof and an internal face of the female connector comprises a second thread, the second thread matching the first thread so that the male and female connectors be threadingly securable together.

In one embodiment, the connection device further comprises securing means for securing the two hemi-tubular bodies together around the first mechanical waveguide.

In one embodiment, an internal face of the two hemi-tubular bodies comprises grooves each for receiving a respective one of the teeth.

In one embodiment, the grooves are pointed.

In one embodiment, the grooves each have a pyramidal shape.

In another embodiment, the grooves each have a conical shape.

In accordance with still another broad aspect, there is provided a mechanical waveguide comprising: an elongated body extending along a longitudinal axis between a proximal end and a distal end, the proximal end being adapted to receive a mechanical wave, the elongated body being adapted to propagate the received mechanical wave from the proximal end to the distal end, and the distal end being adapted to transmit at least a portion of the propagated mechanical wave into a medium surrounding the distal end.

In one embodiment, the elongated body has a cylindrical shape.

In one embodiment, the elongated body has a constant diameter along the longitudinal axis.

In one embodiment, the elongated body has a varying diameter along the longitudinal axis.

In one embodiment, the distal end is adapted to cross at least one of a fibrotic tissue and a calcified tissue contained within an occlusion.

In one embodiment, the distal end is adapted to at least one of tunnel, cross, cleave, break, penetrate in and create a path within an occlusion.

In one embodiment, the distal end is adapted to create a tension wave in the medium surrounding the distal end and create a cavitation effect within the medium.

In one embodiment, at least a section of the elongated body is made of a biocompatible material.

In one embodiment, at least a section of the elongated body is coated with a biocompatible material.

In one embodiment, at least a section of the elongated body is dispersive.

In one embodiment, the elongated body is non-dispersive.

In one embodiment, at least a section of the elongated body is sized to be insertable into a blood vessel of a body.

In one embodiment, the elongated body is made of a single material.

In one embodiment, the elongated body is made of several materials.

In one embodiment, at least a section of the elongated body is provided with a coating having an acoustic impedance being different from an acoustic impedance of the elongated body.

In one embodiment, at least a section of the elongated body has a low-friction coating.

In one embodiment, the low friction coating is made of a hydrophobic material.

In one embodiment, the low friction coating is made of a hydrophilic material.

In one embodiment, the low friction coating is made of polytetrafluoroethylene.

In one embodiment, at least a section of the elongated body is provided with a surface finish adapted to reduce friction.

In one embodiment, a section of the elongated body is adapted to be one of manipulated by a user and be secured to a grabbing tool.

In one embodiment, at least a section of the elongated body is made of one of a flexible material and an elastic material.

In one embodiment, at least a section of the elongated body is made of a low attenuation material.

In one embodiment, the low attenuation material comprises one of stainless steel, aluminum, aluminum alloy, titanium, titanium alloy, nitinol, and fused quartz.

In one embodiment, the titanium alloy comprises one of Ti-6Al-4V and Ti-11.5Mo-6Zr-4.5Sn (Beta III titanium).

In one embodiment, at least a section of the elongated body is heat treated.

In one embodiment, the heat treatment is annealing.

In one embodiment, at least a section of the elongated body has a low attenuation microstructure.

In one embodiment, at least a section of the elongated body is adapted to withstand stress and strain generated by a propagation of a mechanical pulse therealong.

In one embodiment, at least a section of the elongated body is adapted to withstand fatigue associated with repetitive passages mechanical pulses.

In one embodiment, cross-sectional dimensions of the elongated body are less than a center wavelength of a mechanical pulse propagating therealong.

In one embodiment, the elongated body has a circular cross-section and a diameter of the elongated body is less than the center wavelength of the mechanical pulse propagating therealong.

In one embodiment, a diameter of the cylindrical elongated member is chosen so as to allow the cylindrical elongated body to withstand a pushing force exerted by a user.

In one embodiment, at least a section of the elongated body is adapted to be inserted into a catheter.

In one embodiment, a cross-section of the at least a section of the elongated body is chosen so as to minimize contact with the catheter.

In one embodiment, a cross-section of the at least a section of the elongated body is one of rectangular and square.

In one embodiment, the at least a section of the elongated body comprises bumps protruding from a lateral surface thereof.

In one embodiment, the proximal end is one of flat, partially rounded and rounded.

In one embodiment, the distal end is coated with one of a hydrophobic material and a hydrophilic material.

In one embodiment, the mechanical waveguide further comprises an acoustic coupler secured at the distal end.

In one embodiment, the mechanical waveguide further comprises a radiopaque marker secured adjacent to at the distal end.

In one embodiment, the radiopaque marker comprises one of a tungsten marker, gold strips, a high-density plating, a high-density ring, a high-density coil and doped polymer jacket with dense metal powders.

In one embodiment, the distal end is one of flat, rounded, partially rounded, and beveled.

In one embodiment, the distal end is shaped to direct the mechanical pulse at least partially radially.

In one embodiment, the distal end has a truncated conical shape.

In one embodiment, the distal end is adapted to focus mechanical energy away from the distal end.

In one embodiment, a given section of the elongated body adjacent to the distal end is one of curved, bent and bendable.

In one embodiment, a diameter of the cylindrical elongated body is comprised between about 0.004 and about 0.035 in.

In one embodiment, a diameter of the distal end is greater than a diameter of a section of the elongated body adjacent to the distal end.

In one embodiment, the elongated body comprises plurality of individual wires.

In one embodiment, the elongated body has a tubular shape.

In one embodiment, a ratio between a length of the elongated body and a diameter of the elongated body is greater than 100.

In one embodiment, the ratio between the length of the elongated body and the diameter of the elongated body is greater than 1000.

In one embodiment, a length of the elongated body is comprised between about 36 in and about 200 in.

In one embodiment, the proximal end is connectable to a source of mechanical waves or pulses.

In one embodiment, the tubular elongated body contained one of fluid and gas.

In one embodiment, the distal end is shaped to focus the mechanical wave away therefrom.

In one embodiment, the distal end has a concave shape.

In one embodiment, a section of the elongated body adjacent to the distal end is split into different regions along the longitudinal axis.

For the purpose of the present description, the expression "narrowband bandwidth" should be understood as a fractional bandwidth smaller than about 10%, and the expression "broadband bandwidth" should be understood as a fractional bandwidth larger or equal to about 10%. The fractional bandwidth is given by the following equation:

$$100*\Theta f/f_c$$

where $f_c$ is the center/peak frequency (i.e. the frequency at which the frequency spectrum is maximum) and $\Theta f$ is the −3 dB bandwidth. The expression "−3 dB bandwidth" should be understood as the frequency bandwidth over which the magnitude of vibration is greater than half the magnitude at the center/peak frequency $f_c$.

Therefore, a broadband signal should be understood as a signal having a broadband frequency bandwidth. Similarly, a broadband source should be understood as a source emitting a signal having a broadband frequency bandwidth.

The bandwidth threshold between narrowband and broadband bandwidths may also be defined in term of Q-factor (i.e. quality factor). The Q-factor is defined as the reciprocal of the fractional bandwidth, i.e. $Q=f_c/\Theta f$. The equivalent Q-threshold between narrowband and broadband bandwidths is equal to about 10. A narrowband source corresponds to a high Q (i.e. ringing) source, i.e. a source having a Q-factor being greater than about 10, while a broadband source corresponds to a low-Q (i.e. damped) source, i.e. a source having a Q-factor being equal to or less than about 10.

For the purpose of the present description, a mechanical wave should be understood as a signal having an arbitrary amplitude, duration, waveform, frequency, and/or the like. For example, a mechanical wave may have a high/low amplitude, a short/long duration, different waveforms, and any frequency content.

For the purpose of the present description, a mechanical pulse should be understood as a short duration mechanical wave. The duration of a mechanical pulse is of the order of $1/f_c$.

Furthermore, a mechanical waveguide should be understood as a waveguide adapted to propagate mechanical waves or pulses along its length. In the present description, the expressions "waveguide", "mechanical waveguide" and "transmission member" may be used interchangeably. The shape and dimension of a waveguide may vary. For example, a waveguide may have a cylindrical shape. The diameter of the waveguide may be constant along its length. Alternatively, the diameter of the waveguide may vary along its length. For example, the diameter of a waveguide may decrease along its length so that the waveguide corresponds to a taper.

BRIEF DESCRIPTION OF THE DRAWINGS

Further features and advantages of the present invention will become apparent from the following detailed description, taken in combination with the appended drawings, in which.

It will be noted that throughout the appended drawings, like features are identified by like reference numerals.

DETAILED DESCRIPTION

Figure 1:
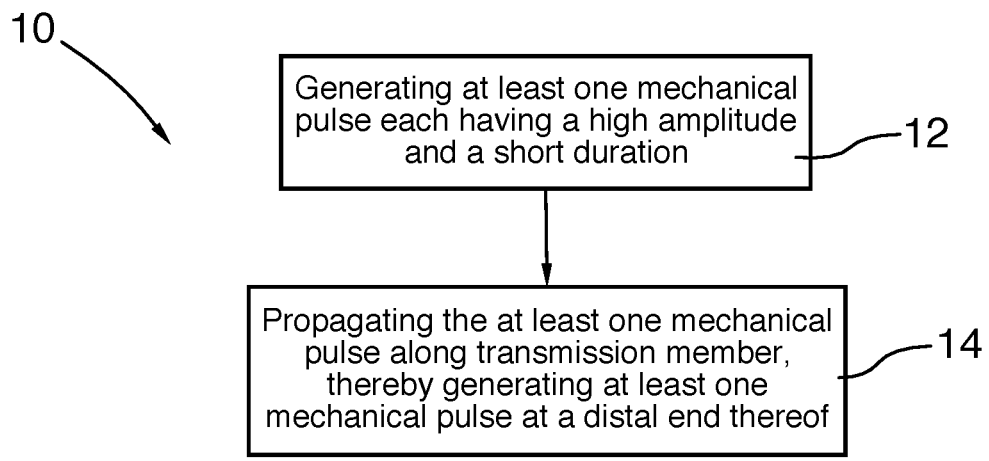
FIG. 1 is a flow chart illustrating a method for generating a mechanical pulse, in accordance with an embodiment.

FIG. 1 illustrates one embodiment of a method 10 for generating and propagating mechanical pulses. In one embodiment, the method may be adapted to treat vascular occlusions, i.e. to cross an occlusion present in a blood vessel such as a vein or an artery or in any other conduct present in a human body. The method 10 may have applications in fields other than the medical field. For example, the method may be used to cross occlusions/obstructions present in a conduct that is used to propagate water or any other fluid.

At step 12, at least one mechanical pulse is generated. Each mechanical pulse has a high amplitude and a short duration.

In one embodiment, the outputs of several sources covering adjacent frequency bands are combined together to generate the mechanical pulse. In one embodiment, the outputs of at least two broadband sources, i.e. the mechanical pulses generated by the at least two broadband sources, are combined together. In another embodiment, the outputs of at least one broadband source and at least one narrowband source are combined together.

In another embodiment, the mechanical pulses are generated by focusing, via a spatial concentrator, the output of a large broadband source toward a focal zone. It should be understood that the outputs of more than one large broadband source may be concurrently focused on the same focal zone.

In a further embodiment, a high amplitude mechanical pulse may be generated by spatially and/or temporally combining mechanical pulses or waves sequentially emitted by a single broadband source using a reverberating cavity. It should be understood that the mechanical pulses generated by more than one broadband source may be spatially and/or temporally combined together by a reverberating cavity to provide the high amplitude mechanical pulse.

In still another embodiment, high amplitude mechanical pulses may be generated by using a dispersive medium to combine the component waves (introduced below in the context of the temporal wave concentrator 62) emitted sequentially by a single broadband source. It should be understood that the mechanical pulses generated by more than one source may be combined together using the dispersive medium.

At step 14, each mechanical pulse is propagated along a transmission member such as a waveguide adapted to propagate mechanical pulses or waves, i.e. a mechanical waveguide. The transmission member extends between a proximal end and a distal end. The transmission member receives the generated mechanical pulse at the proximal end and the mechanical pulse propagates along the transmission member up to the distal end. When it reaches the distal end, the mechanical pulse is transmitted at the distal end, which creates a displacement of the distal end and a mechanical pulse that propagates in the medium surrounding the distal end of the transmission member away from the distal end. In one embodiment, substantially all of the mechanical pulse is transmitted at the distal end of the transmission member. In another embodiment, only a portion of the mechanical pulse is transmitted at the distal end of the transmission member depending, among other things, on the acoustical impedance continuity at the interface between the distal end and the surrounding medium.

In one embodiment, the mechanical pulse has a center frequency $f_c$ comprised between about 20 kHz and about 10 MHz. In one embodiment, the amplitude of the mechanical pulse when reaching the distal end of the transmission member is comprised between about 10 MPa and about 1000 MPa. In one embodiment, the duration of the mechanical pulse when reaching the distal end of the transmission member is in the order of $1/f_c$.

In one embodiment, the method may be adapted to treat vascular occlusions, i.e. to cross an occlusion present in a blood vessel. In this case, at least a section of the transmission member is positioned within the vessel so that its distal end be adjacent to the occlusion. For example, the distal end of the transmission member may be in physical contact with the occlusion. When a mechanical pulse reaches the distal end of the transmission member, the distal end will impact onto the occlusion and transmits the mechanical pulse in the occlusion itself. If the distal end of the transmission member is not in physical contact with the occlusion, the mechanical pulse is transmitted in the medium present between the occlusion and the distal end, e.g. blood, and the transmitted mechanical pulse can propagate up to the occlusion. The mechanical pulse allows cracking, eroding cleaving, tunneling and/or breaking the occlusion and further allows the distal end of the transmission member to cross the occlusion as the distal end is moved farther within the vessel.

In one embodiment, the method further comprises a step of amplifying the amplitude of the mechanical pulse. In an embodiment in which a temporal concentrator is present, the mechanical wave becomes a mechanical pulse of which the amplitude is greater than that of each component wave of the mechanical wave. In an embodiment in which a spatial concentrator is present, the amplitude of a mechanical pulse or wave is increased while propagating through the spatial concentrator. In another embodiment in which a spatial concentrator is present, different mechanical waves or pulses combine together to generate a greater amplitude mechanical wave or pulse, i.e. the different mechanical waves or pulses add to each other.

Figure 2:
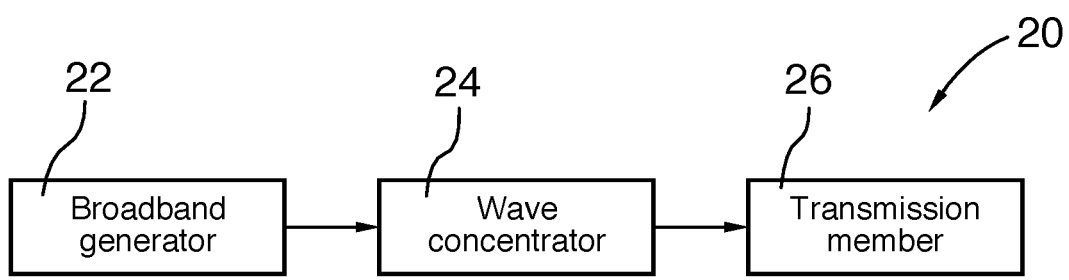
FIG. 2 is a block diagram of a system for generating a mechanical pulse, in accordance with an embodiment.

FIG. 2 illustrates one embodiment of a system 20 that may be used to perform the method 10. The system comprises a broadband generator 22, a concentrator 24 operatively connected to the mechanical pulse generator 22, and a transmission member 26 operatively connected to the concentrator 24.

The broadband generator 22 comprises at least one broadband source adapted to generate mechanical waves. The generated mechanical waves are broadband and each have a substantially low amplitude. The mechanical waves are propagated through the concentrator 24 in which their amplitude increases so that the concentrator 24 outputs mechanical pulses which have a greater amplitude than that of the mechanical waves. If the concentrator 24 is a temporal concentrator, at least two component waves of the mechanical waves interact together while propagating along the temporal concentrator to generate at least one mechanical pulse at the output of the temporal concentrator so that the amplitude of the mechanical pulse is greater than that of the mechanical waves and the duration of the mechanical pulse is shorter than that of the mechanical waves. The mechanical pulses are then transmitted into the transmission member 26 at a proximal end thereof and they propagate along the transmission member 26 up to the distal end thereof. The transmission of the mechanical pulses at the distal end of the transmission member 26 creates mechanical pulses that displace the distal end of the transmission member 26 and then propagate in the medium surrounding the distal end of the transmission member 26 away from the distal end of the transmission member 26.

In one embodiment, the transmission member 26 is adapted to be inserted into a blood vessel, a catheter, or the like. In this case, the transmission member 26 is sized and shaped to slide into the blood vessel or the catheter. In one embodiment, the transmission member 26 is made of a flexible material so that it may be bent to follow curvatures of the blood vessel or the like.

In one embodiment, the concentrator 24 comprises at least two concentration stages. For example, a first concentration stage may consist of a spatial wave concentrator while a second concentration stage may consist of a temporal wave concentrator. It should be understood that any adequate concentrator adapted to increase the amplitude of the mechanical pulses may be used. It should also be understood that when no temporal concentrator is present, the broadband sources are adapted to generate mechanical pulses. It should also be understood that, when a temporal concentrator is present, the broadband sources are adapted to generate mechanical waves which become a mechanical pulse after propagating in the concentrator 24. It should be understood that the order of the concentration stages may be reversed so that the first concentration stage comprises a temporal concentrator and the second concentration stage comprises a spatial concentrator.

In an example in which no temporal concentrator is present, a spatial wave concentrator may be adapted to focus the mechanical pulse emitted by a large broadband source on the input of the transmission member 26 which has a cross-sectional size that is less than the emission surface of the large broadband source. In another example, a spatial wave concentrator may be adapted to combine and focus the mechanical pulses generated by at least two different broadband sources. The emission time of the mechanical pulses emitted by the broadband sources are chosen so that the mechanical pulses combine together so as to create a single mechanical pulse of which the amplitude is greater than that of the mechanical pulses generated by the broadband sources.

In another example, a spatial wave concentrator may comprise a tapered waveguide.

An example of an adequate temporal mechanical wave concentrator is described in US Patent Application No. 2013/0158453. The temporal wave concentrator comprises an elongated waveguide having dispersive properties that are chosen so that the component waves of a mechanical wave, having a given amplitude and a given duration, propagates therein and combine together at the end of the elongated waveguide to create a pulse having an amplitude that is greater than the given amplitude of the mechanical wave and a duration that is less than the given duration of the mechanical wave.

While in the illustrated embodiment, it is positioned between the broadband generator 22 and the transmission member 26, the person skilled in the art will understand that the wave concentrator 24 may be positioned at the distal end of the transmission member 26. For example, a spatial concentrator such as a taper may be positioned at the distal end of the transmission member 26. The taper may be integral with the transmission member 26, i.e. the transmission member 26 may comprise a tapered section at its distal end.

Figure 3:
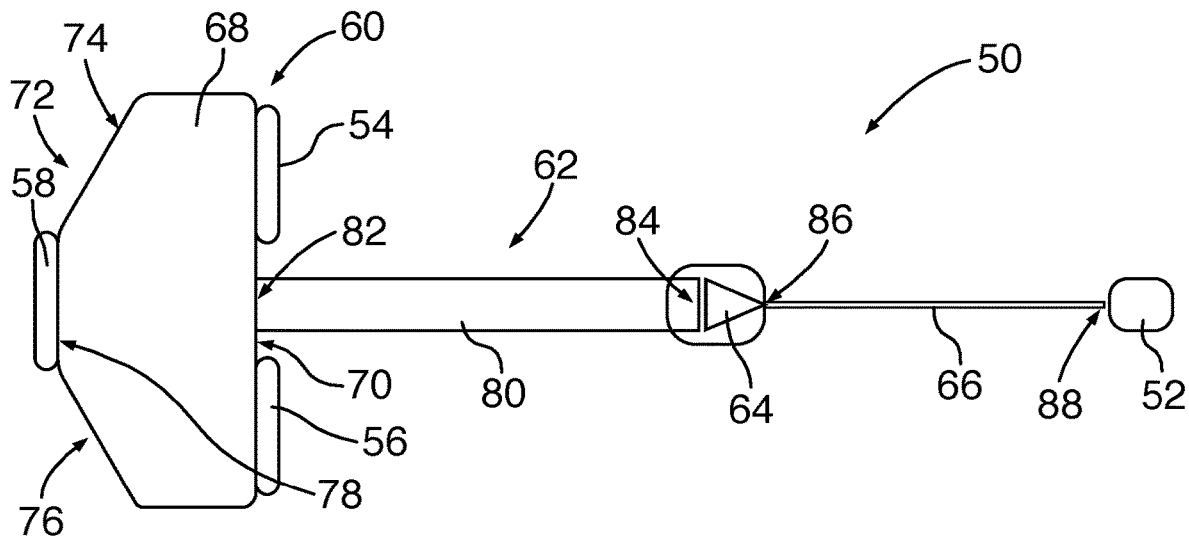
FIG. 3 illustrates a system for generating mechanical pulses comprising a reflecting concentrator, a time concentrator, a taper concentrator, and a transmission member, in accordance with an embodiment.

FIG. 3 illustrates one exemplary system 50 for generating and propagating mechanical waves. In this example, the system 50 is adapted to treat an occlusion 52 that may be present in a blood vessel (not shown) and the mechanical pulses generated by the system 50 are adapted to crack, erode, cleave, tunnel and/or break the occlusion 52.

The system 50 comprises three broadband sources 54-58, a first spatial wave concentrator 60, a temporal wave concentrator 62, a second spatial wave concentrator 64, and a transmission member such as an ultrasound waveguide 66 adapted to propagate mechanical pulses. The system further comprises at least one controller (not shown) for powering and controlling the broadband sources 54-58 so as to control the characteristics of the mechanical waves generated by the broadband sources 54-58. In one embodiment, the elements 54 and 56 are part of a same broadband source having an annular shape.

The first spatial wave concentrator 60 comprises a reflector 68 that extends between a distal or transmission face 70 and a proximal or reflection face 72. In the illustrated embodiment, the transmission face 70 is substantially planar and the broadband sources 54 and 56 are operatively connected to the transmission face 70. It should be understood that the transmission face 70 may not be planar.

The reflection face 72 comprises three sections, i.e. sections 74-78. The sections 74 and 76 are sloped and they each face a respective one of the first and second broadband sources 54 and 56. The angle between the first section 74 and the transmission face 70 is chosen so that mechanical waves emitted by the first broadband source 54 are reflected towards a focal zone such as the center of the transmission face 70. It should be understood that the focal zone may be located on the transmission face 70 at a location other than the center of the transmission zone 70. Similarly, the angle between the second section 76 and the transmission face 70 is chosen so that mechanical waves emitted by the second broadband source 56 are reflected towards the focal zone of the transmission face 70. The section 78 is substantially planar and parallel to the transmission face 70. It should be understood that the section 78 may not be planar. Furthermore, the section 78 faces the center of the transmission face 70. The size and shape of the third section 78 are chosen so as to receive the third broadband source 58. For example, the third section 78 may be rounded such as concave or convex to accommodate a rounded source such as a source having an emission end being convex or concave, respectively.

While the illustrated transmission face 70 is planar, it should be understood that other configurations may be possible. For example, the transmission face 70 may comprise rounded sections such as concave sections and/or convex sections to accommodate rounded sources. For example, the transmission face 70 may comprise rounded recesses defining concave receiving sections each for receiving a respective source 54, 56 having a convex emission end. In another example, the transmission face 70 may comprise rounded protrusions defining convex receiving sections each for receiving a respective source 54, 56 having a concave emission end.

Similarly, the focal zone 82 may be planar for accommodating a waveguide 80 having a planar end 82. In another embodiment, the focal zone may be rounded for coupling the combined mechanical waves into a waveguide 80 having a rounded end 82. For example, the transmission face 70 may comprise a rounded recess at the focal zone defining a concave coupling section for accommodating a waveguide 80 having a convex end 82. In another example, the transmission face 70 may comprise a rounded recess at the focal zone defining a convex coupling section for accommodating a waveguide 80 having a concave end 82. The temporal wave concentrator 62 is adapted to receive and combine together at least two component waves of a mechanical wave having a given amplitude into at least one mechanical pulse having an amplitude that is greater than the given amplitude. In one embodiment, the temporal wave concentrator 62 comprises a dispersive waveguide 80 such as the ultrasound waveguide described in the US Patent Application No. 2013/0158453. The dispersive waveguide 80 extends between a proximal end 82 and a distal end 84. The proximal end 82 is adjacent to the spatial wave concentrator 60 so as to be operatively connected thereto, and substantially faces the center of the propagation face 70. The properties of the dispersive waveguide 80 are chosen so that the waveguide 80 be adapted to combine component waves of the mechanical wave emitted by the broadband sources 54-58 into greater amplitude mechanical pulses, as described below.

The temporal wave concentrator 62 comprising the dispersive waveguide 80 operates as follows. Any mechanical wave can be decomposed into a finite sum of component waves. The component waves each include a function in time and a function in space. Specifically, each component wave has an associated frequency, magnitude, phase in time and an associated deformation field in space. A specific shape of the deformation field corresponds to a mode of the waveguide. In the present description we consider that a component wave has an associated frequency, an associated magnitude, an associated phase, and an associated mode of the waveguide. As a consequence, two component waves may have a same frequency and excite different modes. Two component waves may also have different frequencies and excite a same mode. In another example, two component waves may have different frequencies and excite different modes. For a mechanical wave traveling in the waveguide 80, a component wave has an associated propagation velocity. When the propagation velocity in the waveguide 80 is function of the frequency and the mode of the component wave, the waveguide is qualified as dispersive. Thus, a dispersive waveguide compels a relative phase difference of the component waves of a mechanical wave, which transforms a pulse into a mechanical wave having a lower amplitude and a longer duration.

When the dispersive properties of a waveguide 80 are adequately chosen, dispersion may be used to generate at one end a mechanical wave of which the component waves have associated phases such that, once phase shift is introduced by the dispersive waveguide 80, the component waves recombine at the other end of the waveguide 80 into a desired mechanical wave such as a greater amplitude mechanical pulse.

Referring back to FIG. 3, the second spatial wave concentrator 64 is operatively connected to the distal end 84 of the dispersive waveguide 80. The second spatial wave concentrator 64 is adapted to increase the amplitude of mechanical pulses that propagate therethrough. In one embodiment, the second spatial wave concentrator 64 comprises a taper which consists of a non-dispersive ultrasound waveguide of which the cross-sectional area decreases along a length thereof. A first or proximal end of the taper 64 is operatively connected to the distal end 84 of the temporal wave concentrator 62 so as to receive mechanical pulses therefrom. As a mechanical pulse propagates along the taper 64, its amplitude increases, and the amplified mechanical pulse exits the taper at a second end thereof.

The transmission member 66 extends between a first or proximal end 86 that is operatively connected to the second or distal end of the second spatial wave concentrator 64, and a second or distal end 88. The transmission member 66 is adapted to receive mechanical pulses at its first end 86 and propagate the mechanical pulses up to its second end 88. When it reaches the distal end 88, the mechanical pulse is at least partially transmitted to generate a transmitted pulse that propagates outside of the transmission member 66. It should be understood that a pulse may also be reflected by the end 88 and propagates back in the transmission member 66 towards the first end 86. The transmitted mechanical pulse corresponds to a mechanical pulse that propagates in the medium surrounding the second end 88 of the transmission member 66 up to the occlusion 52. The transmitted pulse further propagates into the occlusion 52, which creates cracks within the occlusion 52, and eventually cleaves or breaks the occlusion 52 into pieces. Also, as the pulse propagates along the transmission member, radial and longitudinal motion is induced at the surface of the transmission member which reduces the friction between the transmission member and surrounding medium and facilitates the longitudinal displacement of the transmission member into the medium, such as when crossing fibrotic tissue within an occlusion.

In an embodiment in which the distal end 88 of the transmission member 66 abuts against the occlusion 52, the transmission member 66 may further be used to break the occlusion 52 and/or drill a hole into the occlusion 52. The transmission of the mechanical pulse at the distal end 88 of the transmission member 66 creates a movement of the distal end 88 of the transmission member 66. During this movement, the distal end 88 of the transmission member 66 nominally first moves towards the occlusion 52 and then moves back into its initial position. It should be understood that the movement may be inversed (i.e. the distal end 88 may first move away from the occlusion 52 and then towards the occlusion 52) depending on the polarity of the mechanical pulse reaching the distal end 88 of the transmission member 66. It should also be understood that the movement could be a complex combination of back and forth motions. When a plurality of distinct mechanical pulses are successively transmitted at the distal end 88 of the transmission member 66, the movement of the distal end 88 may be seen as a jack-hammer movement which may be used to cross the occlusion 52.

As the distal end 88 of the transmission member 66 recesses (i.e. goes away from the occlusion), a tension wave is created in the medium surrounding the distal end 88 which may create a cavitation effect. If the medium is a fluid and since a fluid cannot withstand tensile forces, the fluid changes phase and vaporizes into microscopic bubbles (void and/or vapor). These bubbles are unstable and may collapse violently inducing powerful shock waves and velocity jets. The erosion capability of the induced shock waves and velocity jets may contribute to the ablation of the occlusion 52.

While in the above description the waveguide 80 is dispersive and the taper 64 and the transmission waveguide 66 are non-dispersive, it should be understood that other configurations may be possible. For example, both the waveguide 80 and the taper 64 may be dispersive. In this case, the person skilled in the art will understand that the component waves combine together to provide a high amplitude mechanical pulse at the distal end of the taper 64 instead of the distal end of the dispersive waveguide 80. In another example, the waveguide 80, the taper 64, and the transmission member 64 are all dispersive. In this case, the component waves combine together to provide a high amplitude mechanical pulse at the distal end 88 of the transmission member 66. In another example, the transmission waveguide 66 and the waveguide 80 are both dispersive while the taper 64 is non-dispersive.

It should be understood that a first section of the transmission member 66 is inserted within the blood vessel which contains the occlusion 52 and a second section of the transmission member 66 is located outside the blood vessel. In one embodiment, at least the first section of the transmission member 66 is adapted to be inserted into a blood vessel. For example, the first section of the transmission member 66 may comprise a biocompatible coating or be made of a biocompatible material.

The following describes the operation of the system 50. A first section of the transmission member 66 is inserted into a blood vessel containing an occlusion 52 so that the distal end 88 of the transmission member 66 is adjacent to the occlusion 52. In one embodiment, the transmission member 66 is positioned so that its distal end 88 substantially abuts against the occlusion 52.

The broadband sources 54-58 are each adapted to emit at least two different component waves, e.g., at least a slower component wave and a faster component wave (relative to the dispersive waveguide). Each component wave emitted by the broadband source 54 propagates from the transmission face 70 within the reflector 68, reflects at the section 74 of the reflection face 72, and propagates back towards a focal zone located at the center of the propagation face 70. Similarly, each component wave emitted by the broadband source 56 propagates from the transmission face 70 within the reflector 68, reflects at the section 76 of the reflection face 72, and propagates back towards the focal zone. Each component wave emitted by the broadband source 58 propagates through the reflector 68 towards the center of the focal zone. Since the proximal end 82 of the dispersive waveguide 80 is positioned at the focal zone, the component waves emitted by the broadband sources 54-58 are transmitted into the dispersive waveguide 80.

The broadband sources 54-58 are operated so that the component waves have substantially the same waveform when reaching the focal zone. It should be understood that the amplitude of the component waves emitted by the broadband sources 54-58 may be different when reaching the focal zone. The emission time for each broadband source 54-58 is chosen so that the component waves reach the center of the transmission face 70 substantially at the same time and are transmitted into the proximal end 82 of the dispersive waveguide 80 substantially at the same time. As a result, the individual component waves emitted by the broadband sources 54-58 combine together at the proximal end 82 of the dispersive waveguide 80 to create a component wave having a greater amplitude than that of the individual component waves. Different greater amplitude component waves emitted by the broadband sources 54-58 propagate along the dispersive waveguide 80 and combine together at the distal end 84 of the dispersive waveguide 80 to form a first mechanical pulse.

For example, the broadband sources 54-58 each emit a first component wave, such as a slower component wave, at an adequate time so that the first component wave combine together to create a first greater amplitude component wave, such as a greater amplitude slower component wave, when reaching the proximal end 82 of the dispersive waveguide 80. After emitting the first component wave, the broadband sources 54-58 each emit a second component wave, such as a faster component wave, at an adequate time so that the second component wave combine together to create a second greater amplitude component wave, such as a greater amplitude faster component wave, when reaching the proximal end 82 of the dispersive waveguide 80.

A constructive recombination occurs when the greater amplitude slower component wave is sent in the dispersive waveguide 80 before the greater amplitude faster component wave, at time intervals that compensate for the relative phase shift introduced by the dispersive waveguide 80. The slower and the faster greater amplitude component waves interact with each other up to the distal end 84 of the dispersive waveguide 80. When the interaction is constructive (i.e. when the component waves have both a positive magnitude or both a negative magnitude), the resultant mechanical wave consists of a greater amplitude mechanical pulse.

As described above, the mechanical waves emitted by the broadband transducers are synchronized so that they combine precisely as they travel down the single or plural concentration stages to generate the high-amplitude mechanical pulse at the distal end 84 of the transmission member 66. The broadband transducers are driven accordingly to produce these timed mechanical waves. The required electrical driving signals can be computed knowing the system behavior or obtained from experimental measurements.

It should be understood that more than two greater amplitude component waves may combine together at the distal end 84 of the dispersive waveguide 80 to create a mechanical pulse. Each of at least two of the component waves has a unique predetermined propagation velocity through the dispersive waveguide 80. It should also be understood that the characteristics of the component waves emitted by the broadband sources 54-58 and the characteristics of the dispersive waveguide 80 are chosen as a function of the desired properties of the mechanical pulse to be generated at the distal end 84 of the dispersive waveguide 80.

In some embodiments, the at least two component waves have an associated frequency and an associated propagation mode of the waveguide. The at least two component waves have different associated frequencies. The at least two component waves have a same associated mode.

In some embodiments, the same associated mode is a single mode of the dispersive waveguide 80.

In some embodiments, the single mode is a fundamental longitudinal mode of the dispersive waveguide 80.

In other embodiments, the at least two component waves have different associated modes. The at least two component waves have a same associated frequency.

Referring back to FIG. 3, the first mechanical pulse propagates from the second end 84 of the dispersive waveguide to the taper 64. In the illustrated embodiment, the taper 64 is a non-dispersive waveguide of which the cross-sectional surface area decreases along a length thereof. Because the taper 64 is non-dispersive, the component waves forming the first mechanical pulse do not separate from one another and the first mechanical pulse propagates along the taper 64. Furthermore, the amplitude of the mechanical pulse increases while it propagates therealong due the decreasing cross-sectional surface area of the taper 64. As a result, a second mechanical pulse is emitted by the taper 64 and the amplitude of the second mechanical pulse is greater than that of the first mechanical pulse.

The second mechanical pulse is coupled into the non-dispersive transmission member 66 in which it propagates up to the distal end 88 where a transmitted mechanical pulse is transmitted in the surrounding medium. As described above, the transmitted pulse propagates up to the occlusion 52 and if the distal end 88 of the transmission member 66 abuts against the occlusion 52, the jackhammer movement created by the multiple mechanical pulses at the end 88 may be used to cross the occlusion 52.

In one embodiment, at least two of the elements constituting the system 50, i.e. the reflector 68, the dispersive waveguide 80, the taper 64, and the transmission member 66, are permanently secured together. For example, at least two of the elements may be welded together.

In the same or another embodiment, at least two of the elements constituting the system 50 are removably secured together using an adequate connector. For example, the taper 64 and the transmission member 66 may be integral together or welded together, and the taper 64 may be removably secured to the temporal concentrator 62. In this case, the assembly formed of the spatial concentrator 64 and the transmission waveguide 6 may be disposable so that this assembly is changed after a procedure while the broadband sources 54-58, the spatial concentrator 60, and the temporal concentrator 62 are used from one procedure to another. It should be understood that other configurations may be possible. For example, only the transmission member 66 may be disposable and removably secured to the spatial concentrator 64.

In one embodiment, an impedance matching element/material may be positioned between two components in order to reduce coupling losses between the two components. For example, one or more layers of impedance matching material may be positioned between the broadband sources 54-58 and the reflector 68. In yet another embodiment, the impedance matching element is positioned between the distal end of the transmission member 66 and the surrounding medium.

In one embodiment, the reflector 68, the dispersive waveguide 80, the taper 64, and the waveguide 66 are all made of a same material in order to reduce losses from impedance mismatches.

It should be understood that at least one of the concentrator 60, 62, and 64 may be omitted and/or the relative position of the concentrator 60, 62, and 64 may be changed. For example, the spatial concentrator 64 may be omitted. In this case, the transmission member 66 may be permanently or removably secured to the temporal concentrator 62. Alternatively, the temporal concentrator may be further omitted and the transmission member 66 may be secured to the spatial concentrator 60. In another example, the spatial concentrator 64 may be positioned at the end of the transmission member 66. In a further embodiment, the temporal concentrator 62 may be omitted and the spatial concentrator 64 may be secured to the spatial concentrator 60. In this case, the broadband sources 54-58 emit mechanical pulses that combine at the input of the spatial concentrator 64 into a greater amplitude mechanical pulse of which the amplitude is further increased while propagating through the spatial concentrator 64 before propagating along the transmission member 66.

While the system 50 uses broadband sources 54-58 such as ultrasound transducers in connection with the concentrator 60 to generate mechanical waves, it should be understood that other configurations may be possible. For example, electromechanical energy such as piezoelectric energy, electromagnetic energy, or magnetostriction energy may be used. As described above, the energy may be concentrated in space, time or both in order to increase the amplitude of the mechanical waves generated by the energy source(s). Spatial concentration configurations may include one or more larger planar/focalized transducer. The transducer(s) can be distributed in a phased array configuration and used with an acoustic lens or an acoustic reflector. Temporal concentrator configurations can use one or more planar/focalized transducer(s) with a dispersive medium or a dispersive waveguide. A reverberating cavity can also be used to combine both spatial and temporal concentration. Any combinations or arrangements of the previous configurations can also be used to achieve similar results. Each transducer composing the broadband generator 22 can have the same bandwidth of operation or can have various bandwidths to achieve the desired level of control.

The followings describe exemplary configurations for the wave concentrator 24.

Figure 4:
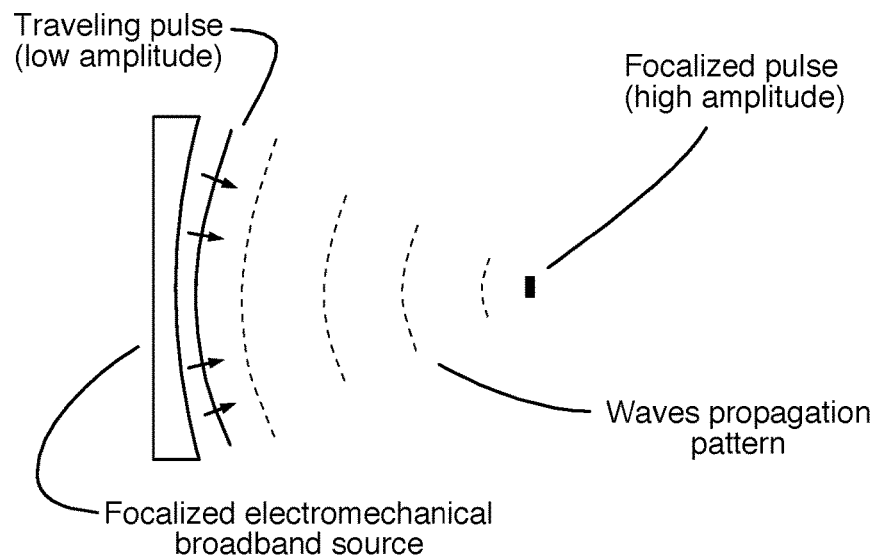
FIG. 4 illustrates a focalized electromechanical broadband source, in accordance with an embodiment.

In one embodiment, one may use a focalized transducer comprising a hemispherical concave emitting surface to direct mechanical waves toward a common focal zone, as illustrated in FIG. 4.

In another embodiment, a phased-array transducer composed of multiple emitting elements that can be individually controlled and disposed in various ways may be used as illustrated by two examples in FIGS. 5a and 5b. Each element can be fired with a different phase/delay to steer, focus and combine the resulting mechanical wavefront. The emitting elements can also be of different shapes. While they are positioned according to a linear configuration in FIG. 5a, the emitting elements are positioned according to a curved configuration in FIG. 5b.

In a further embodiment, an acoustic lens may be used to take advantage of the difference in wave velocity between two media to redirect mechanical waves, as illustrated in FIG. 6a. In order to focus mechanical waves using an acoustic lens, the interface between the two media has a shape similar to the one described for a focalized transducer.

In one embodiment, an acoustic reflector adapted to reflect incident mechanical waves toward the same focal zone may be used as illustrated in FIG. 6b.

Figure 7:
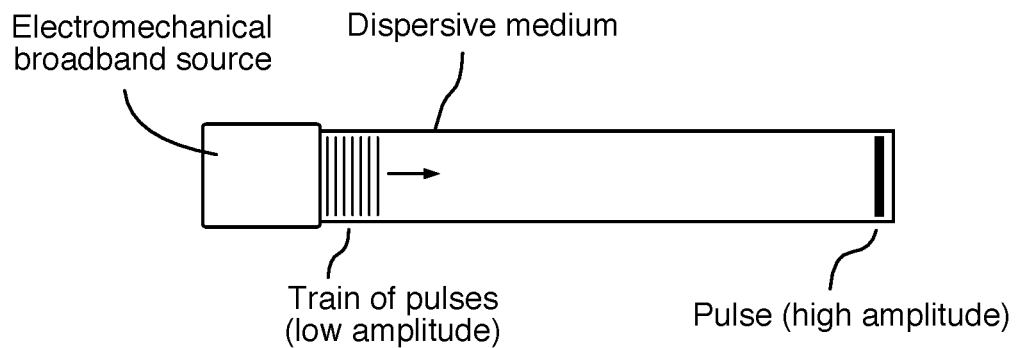
FIG. 7 illustrates an electromechanical broadband source cooperating with a dispersive medium, in accordance with an embodiment.

In another embodiment, one may use a temporal concentrator configuration taking the form of a dispersive medium having a gradient in acoustic wave velocity which is obtained by the generation of a gradient in at least one of its mechanical property, as illustrated in FIG. 7. By properly timing the emission of the component waves composing the input mechanical wave, it is possible to produce a high amplitude mechanical pulse at a desired location by constructive interference. In one embodiment, the dispersive properties of the dispersive medium are due to the geometry of the waveguide instead of the properties of the medium.

Figure 8:
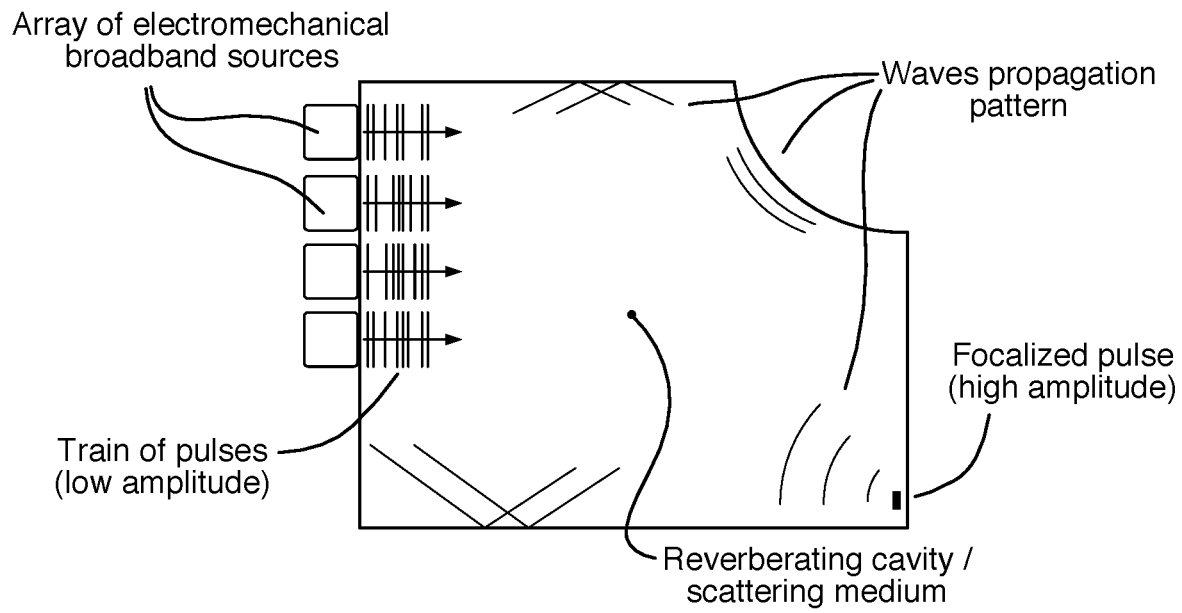
FIG. 8 illustrates an array of electromechanical broadband sources cooperating with a multi-scattering/reverberating medium, in accordance with an embodiment.

In a further embodiment, a configuration combining a spatial concentrator and a temporal concentrator can also be used. This configuration can take the form a reverberating cavity such as a multi-scattering medium, as illustrated in FIG. 8. A reverberating cavity takes advantage of the multiple reflections inside a cavity to spatially and temporally focus mechanical waves toward a desired location using a single or an array of transducers.

Figure 9:
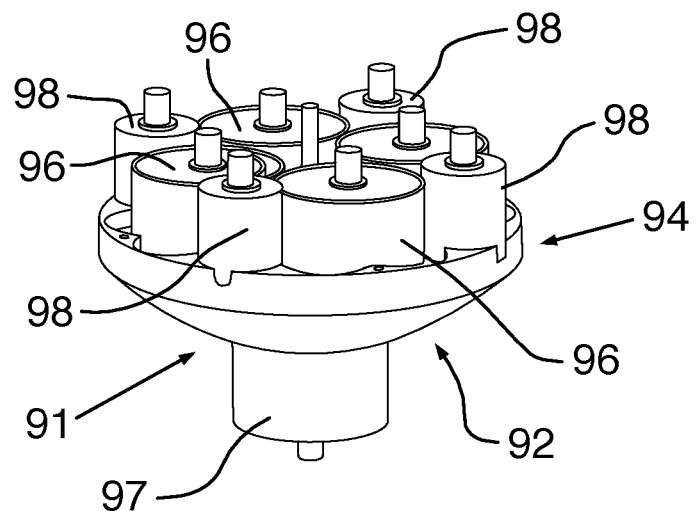
FIG. 9 is a perspective view of a spatial concentrator adapted to combine the mechanical waves emitted by nine electromechanical transducers, in accordance with an embodiment.
Figure 10:
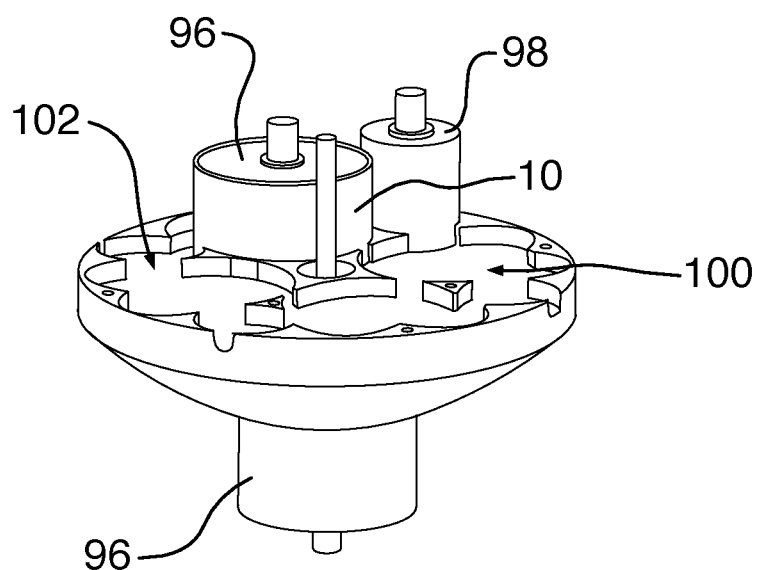
FIG. 10 is a perspective view of the spatial concentrator of FIG. 9 from which six electromechanical transducers have been removed.
Figure 11:
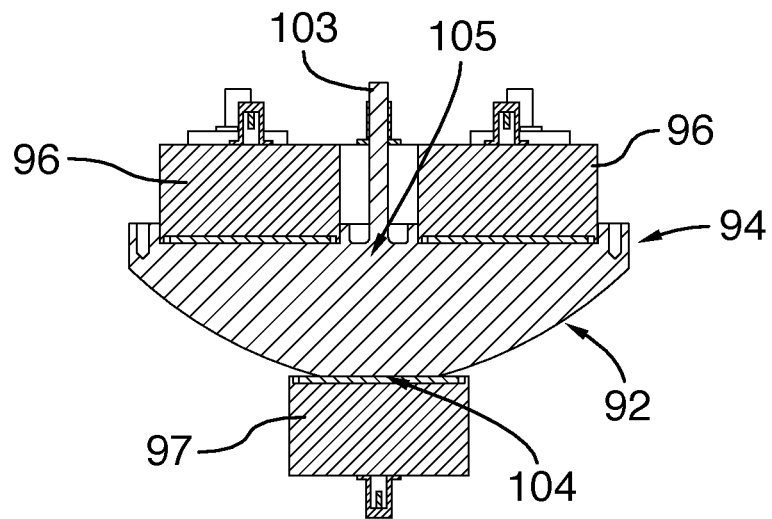
FIG. 11 is a cross-sectional view of the concentrator of FIG. 9.

FIGS. 9-11 illustrate an exemplary spatial concentrator 91 that is adapted to combine together mechanical waves emitted by nine broadband sources such as nine piezoelectric transducers. It should be understood that the concentrator 91 may be used to combine mechanical waves emitted by sources other than broadband sources and that the number of sources is exemplary only. In this example, the spatial concentrator 91 comprises a truncated parabolic section 92 and a cylindrical section 94, and is adapted to receive five piezoelectric transducers 96 and 97 of a first type and four piezoelectric transducers 98 of a second and different type. For example, the piezoelectric transducers 96 and 97 may be cylindrical transducers having a diameter of about 2 inches while the piezoelectric transducers 98 may be cylindrical transducers having a diameter of about one inch. It should be understood that the number of transducers may vary as long as the system includes at least one transducer. For example, the system may comprise two or more concentric annular transducers. It should also be understood that the number of transducer types may also vary. For example all of the transducers may be identical.

As illustrated in FIG. 10, protrusions project from the top face of the cylindrical section 94 to define four recesses 100 and four recesses 102. Each recess 100 is sized and shaped to receive a corresponding piezoelectric transducer 96 while each recess 102 is adapted to receive a corresponding piezoelectric transducer 98. A waveguide 103 such as a dispersive waveguide is secured to the cylindrical section 94.

It should be understood that the recesses 100 and 102 may be omitted. For example, the top face of the cylindrical section 94 may be substantially planar and any adequate means for securing removably or not the transducers 96 and 98 to the planar top face of the cylindrical section 94 may be used.

As illustrated in FIG. 11, the parabolic section 92 comprises a truncated portion 104 located at the apex of the parabolic section 92. The truncated portion 96 is substantially flat, and it is sized and shaped to receive the piezoelectric transducer 97. The piezoelectric transducer 97 is positioned on the truncated portion 106 so that its longitudinal axis be substantially aligned with the longitudinal axis of the waveguide 103. As a result, mechanical waves emitted by the piezoelectric transducer 97 propagate through the concentrator 91 and are transmitted into the waveguide 104. The curvature of the parabolic face of the parabolic section 92 and the position of the recesses 100 and 102 are chosen so that the mechanical waves emitted by each piezoelectric transducer 86, 88 propagate through the concentrator 91, reflect at the parabolic face of the parabolic section 92, and then propagate towards a focal zone 105. A first end of the waveguide 103 is positioned at the focal zone 105 so that the mechanical waves generated by a piezoelectric transducer 96, 98 be coupled into the waveguide 103.

The piezoelectric transducers 96, 97, and 98 emit a respective mechanical wave each at a time chosen so that the different mechanical waves arrive substantially concurrently at the focal zone. The mechanical waves emitted by the transducers 96 and 98, after reflecting at the parabolic face, focus at the focal zone and combine together with the mechanical wave emitted by the transducer 97 to generate a mechanical wave having a greater amplitude than that of the mechanical wave emitted by each piezoelectric transducer 96, 97, and 98 alone.

In an embodiment in which the waveguide 103 is a dispersive waveguide acting as a temporal concentrator, the piezoelectric transducers 96, 97, and 98 may be controlled to first emit slower component waves which combine at the focal zone 105 to generate a greater amplitude slower component wave which is transmitted into the dispersive waveguide 103 and propagate therealong. The piezoelectric transducers 96, 97, and 98 are further controlled to subsequently emit faster component waves which combine at the focal zone 105 to generate a greater amplitude faster component wave which is coupled into the dispersive waveguide 103 and propagate therealong. The faster and slower greater amplitude component waves combine together at the second end of the dispersive waveguide to create a desired mechanical pulse having an amplitude that is greater than that of the faster and slower greater amplitude wave components.

In one embodiment and in order to maximize the spatial concentration of the mechanical waves at the focal zone 105, the distance of propagation of the mechanical wave within the concentrator 91 is minimized, the incident angle at the parabolic surface of the section 82 is minimized, the surface emission is maximized, and/or the operating wavelength is kept as short as possible for the following reasons. The spatial focusing gain is related to the emitting surface A divided by the distance of propagation d and the operative wavelength $\lambda$, i.e. Gain$\approx$A/(d$\lambda$). Other wave propagation phenomena may be considered when mechanical waves travel in a solid medium. For example, mode conversion (e.g., longitudinal into shear) may occur in a solid medium when a mechanical wave is reflected by a boundary interface such as the parabolic surface of the section 92. This mode conversion is related to the angle between the incident wave and the boundary interface. Since they are reflected at an angle different than longitudinal waves, shear waves do not focus at the same zone than that of the longitudinal waves. Therefore, part of the input signal may be lost or trapped when mode conversion is present at a certain extent. Also, at some operative wavelengths the mechanical wavefront does not travel in a straight line but spreads in space due to diffraction. The longer distance a wavefront travels, the more it spreads in space. Therefore and in order to maximize the spatial concentration, the distance of propagation may be kept as short as possible to limit the spreading of the wavefront. Similarly, the incident angle at a parabolic surface may be kept as low as possible to limit mode conversion. The surface emission may also be large. Furthermore, the operative wavelength may be reduced when possible to minimize the aforementioned deleterious effects.

In one embodiment, the transducers 96, 97, and 98 are planar piezoelectric transducers, i.e. their emission surface is planar. Such planar piezoelectric transducers are less expensive than piezoelectric transducers having a non-planar emission surface. Furthermore, it is easier to couple their emission face with the spatial concentrator 91. Moreover taking advantage of a parabolic geometry of the spatial concentrator 91 and by distributing the transducers 86-88 on the top surface symmetrically around the main axis, the person skilled in the art will understand that the control electronics is simplified since the same emitting electronic signal may be used by similar transducers and since there is no need for introducing any phase delay. For example, a same electronic signal may be used to control the four transducers 96 as they constitute a single channel.

In another embodiment, the transducers 96-98 may not be planar. For example, they may be focused transducers. In another example, they may be asymmetrically distributed about the axis of the concentrator 91. In a further example, the transducers 96 and 98 may not be on the same planar surface.

In one embodiment, truncating an area of the parabolic surface reduces the focalization gain for the component waves emitted by the transducers 96 and 98. However, the addition of the transducer 97 on the truncated portion of the section 92 allows increasing the focalization gain with respect to the focalization gain that would be obtained if the transducer 97 would not be present and the parabolic section 92 would not be truncated. In one embodiment, the distance between the focal zone 105 and the truncated section 104 together with its surface area are adequately chosen. Indeed, according to the operative wavelength and the size of the targeted focal zone, there are an optimal distance and surface area that will maximize the spatial concentration of the transducer used on the truncated section.

In one embodiment, the concentrator 91 is designed using the geometric relations of a parabola and the theory of light propagation as a first hypothesis. Then, a numerical finite element model is developed. Once the proper parameters (such as propagating medium, boundary conditions, excitation conditions, and/or meshing) have been determined, this model is used to evaluate the impact of various geometrical parameters on the amplification factor at the focal zone. For example, different shapes, parabolic or not, emission surface area, emission zones distribution and concentrator thickness are evaluated. Furthermore, subsequent numerical models can be developed and used to evaluate the interaction and integration of the concentrator with other components of the system.

In one embodiment, a layer of impedance matching material such as glycerin may be introduced between the concentrator 91 and the transducers 96-98 to reduce coupling losses. Furthermore, the waveguide 103 is mechanically connected to the concentrator 91 at the focal zone 105. For example, welding may be used as a mechanical connection.

While FIGS. 9-11 illustrate cylindrical transducers having a planar emission surface, it should be understood that transducers having a different shape may be used. For example, the shape of the transducers may be annular, hexagonal, square, triangular, circular, or the like.

It should also be understood that the number and location of the transducers 96-98 relative to the concentrator may vary. For example, while the concentrator 91 comprises a single planar portion located on the parabolic surface for receiving the transducer 97, i.e. the truncated portion, the person skilled in the art will understand that the parabolic surface may comprise more than one planar portion. Each planar portion is adapted to receive a respective transducer that will emit mechanical waves towards the focal zone 105. The portions of the parabolic surface located between planar portions may then be used to reflect mechanical waves emitted by transducers positioned on top of the concentrator towards the focal zone 105.

It should be understood that the concentrator 91 may be made of any adequate material in which mechanical waves may propagate. For example, the concentrator 91 may be made of glass, lead, fluid, gas, liquid metal, stainless steel, titanium, nitinol, etc.

While the transducers 96-98 are provided with a planar emission surface, it should be understood that other configurations are possible. For example, the transducers may be provided with a concave emission surface. In this case, the recesses also have a convex shape matching that of a respective concave transducer to accommodate their respective concave transducer. The transducers 96-98 can also be used with an acoustic lens.

Referring back to the transmission member 66, the person skilled in the art will understand that the function of the transmission member 66 is to propagate high amplitude mechanical pulses from its proximal end 86 to its distal end 88. The proximal end 86 is located outside a patient and is permanently or removably connected to the spatial concentrator 64. The distal end 88 is to be inserted into a blood vessel of the patient with or without a catheter.

In one embodiment, the transmission member 66 is made of a single material. In another embodiment, the transmission member 66 may be made of different materials. For example, the transmission member 66 may comprise a first section adjacent to the proximal end 86 and adapted to remain outside of the patient, and a second section adjacent to the distal end 88 and adapted to be inserted into a blood vessel of the patient. In this case, the first section may be made of a first material adapted to propagate high amplitude mechanical pulses while the second section may be made of a second and different material that is also adapted to propagate high amplitude pulses and that is also biocompatible.

In one embodiment, the second section of the transmission member comprises a low-friction coating (e.g., a hydrophobic coating, a hydrophilic coating, polytetrafluoroethylene (PTFE) coating, etc.) or specialized surface finish to reduce friction.

In one embodiment, the second section of the transmission member comprises a low/high acoustical impedance coating, as compared to the acoustical impedance of the transmission member core, to entrap energy in the transmission member core and prevent, or at least reduce, energy leakage. Examples of low/high acoustical impedance materials comprise tungsten, aerogel, gas entrapping jacket and the like.

In one embodiment, the second section of the transmission member comprises a low/high acoustical impedance coating and a low-friction coating, the low-friction coating covering completely or partially the low/high acoustical impedance coating.

In one embodiment, the transmission member 66 may further comprise a third section located between the first and second sections. The third section is adapted to be manipulated by a user such as an interventional physician or to receive a grabbing tool such as a torquer.

In one embodiment, the first, second and/or third section are made of a flexible or elastic material presenting substantially no plastic deformation as the second section follows the tortuous path within the blood vessel leading to the occlusion or as the third section is manipulated by the user.

In one embodiment, the transmission member 66 is made of the same material as that of the element to which its proximal end is secured to ensure an improved coupling of the mechanical pulses into the transmission member 66 and therefore reduce coupling losses.

In one embodiment, the transmission member 66 is made of a low-attenuation material such as stainless steel, aluminum or aluminum alloys, titanium or titanium alloys such as Ti-6Al-4V or, Ti-11.5Mo-6Zr-4.5Sn (Beta III titanium), nitinol, fused quartz or the like. In one embodiment, a heat treatment such as annealing may be applied to at least a portion of the transmission member 66.

In one embodiment, the transmission member 66 has a low-attenuation microstructure that is achieved through one or a series of heat treatment and heat or cold working.

In one embodiment, the transmission member 66 is made of a material having good mechanical properties such as good tensile strength and good torque transmission and good kink resistance.

In one embodiment, the transmission member 66 is adapted to withstand the high stress/strain generated by the mechanical pulse propagating therealong. In the same or another embodiment, the transmission member 66 is adapted to withstand the fatigue associated with the repetitive passage (cycling) of the mechanical pulses.

In one embodiment, the cross-sectional dimension of the transmission member 66 such as the diameter of a cylindrical waveguide is small compared to the center wavelength of the mechanical pulse propagating therealong so that the transmission member 66 is non-dispersive or weakly dispersive in order to reduce energy leakage.

In one embodiment, the cross-sectional dimension of the transmission member 66 such as the diameter of a cylindrical transmission member is large enough to allow the transmission member 66 to withstand a pushing force exerted by a user and required to advance the distal end 88 along the blood vessel or within the catheter and into the occlusion, and to allow a safe and effective control of the distal end 88.

In one embodiment, the outer surface of the transmission member 66 or at least the second section of the transmission member 66 features microscopic details such as fine threads or has some kind of coating, which could entrap microbubbles acting as a shielding layer preventing energy leakage.

In an embodiment in which the transmission member 66 is inserted into a catheter, the cross-sectional shape of the transmission member 66 is adapted to minimize the physical contact within the catheter to minimize energy leakage and/or friction. For example, if the catheter comprises a circular cavity in which the transmission member 66 is inserted, the transmission member 66 may have a square cross-section to reduce the contact with the catheter to the four corners of the square. In another embodiment, the external surface of the transmission member 66 could be provided with small features such as bumps along its length to minimize the contact with the catheter.

In one embodiment, the proximal end 86 of the transmission member 66 and/or the first section of the transmission member 66 is not coated and is surrounded by ambient air since there is substantially no boundary friction or energy leakage to prevent or reduce.

Figure 12:
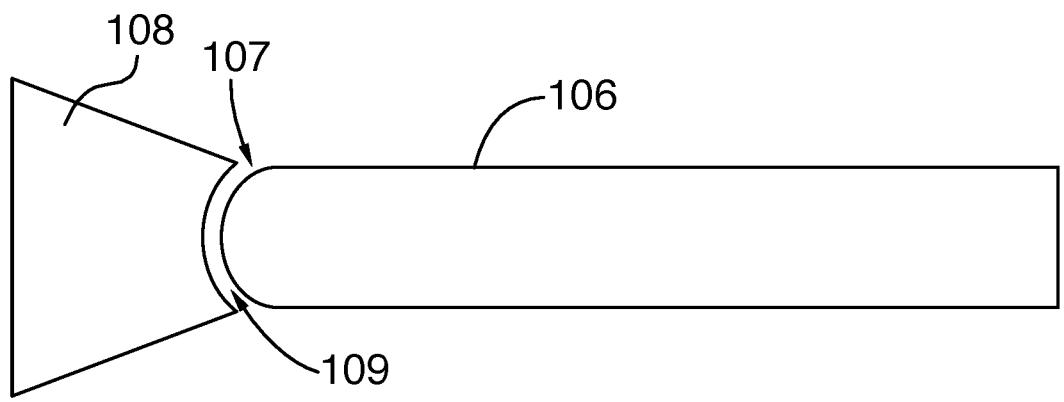
FIG. 12 illustrates a connection between a rounded-end transmission member and a taper; in accordance with an embodiment.

It should be understood that the proximal end 86 of the transmission member 66 may be provided with any adequate shape. For example, the proximal end 86 may be substantially flat. In another embodiment, the proximal end may be rounded as illustrated in FIG. 12 which illustrates a waveguide 106 having a rounded proximal end 107 which protrudes from the waveguide 106. The element 108 to which the waveguide 106 is to be secured comprises an inwardly rounded end 109 which match the rounded end 107 of the waveguide 106. Such a configuration improves the mating of the waveguide 106 to the element 108 and may compensate for misalignment.

In one embodiment, the proximal end 86 of the transmission member 66 serves as an entry point to slide in an over-the-wire equipment such a catheter, a balloon or a stent.

In one embodiment, the proximal end 86 of the transmission member 66 is made of a material presenting an acoustical impedance that is compatible with that of the element to which it is secured, such as the spatial concentrator 64.

The distal end 88 of the transmission member 66 is used to emit the mechanical pulses from the transmission member 66 core toward the occlusion 52. The distal end 88 may also be used to create a path and navigate through the occlusion 52, enlarge the diameter of the path, and/or orient the direction of the emitted mechanical pulses.

In an embodiment, in which the transmission member 66 is to be inserted into a catheter, the distal end 88 of the transmission member 66 may be designed as to facilitate its introduction into the catheter toward the occlusion. In one embodiment, a hydrophobic coating may be applied at the distal end 88 of the transmission member to flush the blood out of the catheter as the distal end 88 advances toward the occlusion 52 and thereby reduce the quantity of blood that surrounds the transmission member 66 which could contribute to energy leakage.

In one embodiment, a hydrophilic coating is added at the distal end 88 of the transmission member 66 to facilitate its introduction in a catheter.

In one embodiment, an acoustic coupler is secured to the distal end 88 of the transmission member 66 in order to increase the energy transmission from the transmission member 66 towards the occlusion 52.

In one embodiment, radiopaque markers such as tungsten, gold strips, high-density plating, high-density ring, high-density coil or doped polymer jacket with dense metal powders are secured to the distal end 88 of the transmission member 66 to serve as references points in order to visualize via X-rays the position of the distal end relative to the occlusion 52 and to other PTA devices.

In one embodiment, the distal end 88 of the transmission member 66 is substantially flat. In one embodiment, the flat surface of the distal end 88 is substantially orthogonal to the outer longitudinal surface of the transmission member 66 that extends along the length thereof in order to maximize the energy output along the longitudinal axis along which the transmission member 66 extends. In another embodiment, the flat surface of the end 88 is beveled or at an angle with respect to that longitudinal axis. Such shape may also propel the wire sideways resulting in a slapping effect that may be used to enlarge the path created within the occlusion or have vessel preparation intention before the use of a balloon during PTA intervention. It should be understood that the distal end 88 may be provided with any adequate shape other than a flat shape. For example, the distal end may be provided with a rounded shape such as a hemispherical shape. The surface of the distal end 88 may be provided with any adequate shape between a rounded shape and a flat shape. For example, the surface of the distal end 88 may be substantially planar with a smoothed or rounded edge to be as atraumatic as possible for biological tissues. In another example, the distal end maybe provided with a shape to focus the mechanical energy away from the distal end 88. This focusing shape could be a concave shape, for example a circular or parabolic shape. This focusing shape could be such as to focus the mechanical pulse along the longitudinal axis of the transmission member, or away from this same axis.

In one embodiment, the distal end 88 of the transmission member 66 may be shaped so as to direct the mechanical pulse at least partially radially. This configuration may be used to create a path in the occlusion 52 with a diameter larger than that of the distal end 88. Moreover, such embodiment may be used to prepare the lesion site prior the use of balloon during a PTA intervention.

Figure 13:
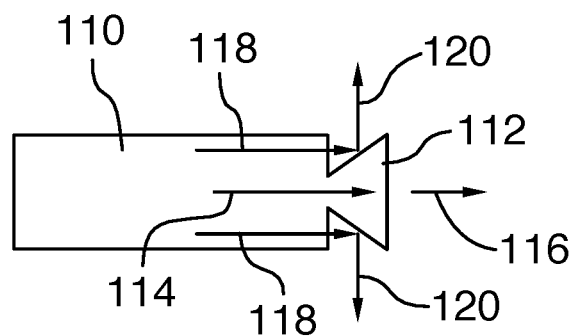
FIG. 13 illustrates an exemplary transmission member provided with a wave-deflecting protrusion at a distal end, in accordance with an embodiment.

FIG. 13 illustrates such a configuration in which a transmission member or waveguide 110 is provided with a distal end adapted to partially emit a radial mechanical wave. A protrusion 112 having a truncated conical shape protrudes from the distal end of the waveguide 112. The protrusion 112 extends between a circular distal wall located away from the waveguide 110 and a circular proximal wall secured to the waveguide 110. A truncated conical wall extends between the circular proximal and distal walls. In the illustrated embodiment, the waveguide 110 and the protrusion 112 are coaxial.

In another configuration, the distal tip of the transmission member could be split into regions along a direction essentially parallel to its longitudinal axis, such that when the mechanical pulse reaches this region it forces the various regions away from the split interface, enabling some redirection of some of the energy in the radial direction. In another configuration, the distal tip of the transmission member could be alternately curved along the longitudinal axis so as to redirect some of the mechanical energy in the radial direction. However, the person skilled in the art will understand that other configurations may be possible.

As illustrated in FIG. 13, the central portion of the mechanical energy schematically represented by arrow 114 propagates through the protrusion 112 to generate a longitudinal mechanical wave schematically represented by arrow 116 that propagates substantially along the longitudinal axis of the waveguide 110 outside of the waveguide 110 towards the occlusion 52. The outer portion of the mechanical energy schematically represented by arrow 118 and adjacent to the outer surface of the waveguide 110 propagates outside of the waveguide 110 and is reflected by the truncated conical wall of the protrusion 112 to generate a radial mechanical wave.

While in the illustrated embodiment, the propagation direction of the radial mechanical wave is substantially orthogonal to that of the longitudinal mechanical wave, it should be understood that other configurations are possible by varying the angle between the waveguide 110 and the truncated conical wall of the protrusion 112. Moreover, such configuration does not need to be symmetrical around the main axis of the ultrasound waveguide.

The person skilled in the art will understand that the amount of energy converted into a radial mechanical wave may be adjusted by adequately varying the surface area of the distal and/or proximal walls of the protrusion 112.

In one embodiment the section of the transmission member 66 adjacent to the distal end 88 may be bent or bendable so a user may apply a permanent or temporary curvature with his fingers, a metallic needle introducer or a tool. A bent at the distal end 88 may be used to steer the transmission member (i.e. to give the transmission member a direction) as it is pushed forward in the blood vessel or in the occlusion and/or to redirect the emitted mechanical pulse.

In one embodiment, the transmission member 66 has a cross-sectional shape and/or cross-sectional dimensions that are substantially constant along a length thereof. For example, the transmission member 66 may have a circular cross-sectional shape of which the diameter is substantially constant along the length thereof. In one embodiment, the diameter of the waveguide 66 is between about 0.004 and about 0.035 in.

In another embodiment, the cross-sectional shape and/or the dimensions of the transmission member 66 may vary along a length thereof. For example, the first section of the transmission member 66 that is adjacent to the proximal end 66 and/or the second section of the transmission member 66 that is adjacent to the distal end 88 may have a cross-sectional shape and/or a dimension different from a third section located between the first and second sections. In another example, the transmission member 66 may comprise at least one tapering section for amplifying mechanical pulses.

For example, the proximal end 86 may be provided with a circular cross-sectional shape having a first diameter while the third section of the transmission member 66 may be provided with a circular cross-sectional shape having a second and different diameter. For example, the first diameter may be greater than the second diameter. In another example, the second diameter may be greater than the first diameter. In one embodiment, the diameter of the transmission member 66 smoothly varies from the first diameter to the second diameter along a given section of the transmission member 66.

In another example, the proximal end 86 may be provided with a first cross-sectional shape while the third section of the transmission member 66 may be provided with a second and different cross-sectional shape. For example, the proximal end 86 may be provided with a square cross-sectional shape while the third section of the transmission member 66 may be provided with a circular cross-sectional shape. In another example, the proximal end 86 may be provided with a hexagonal cross-sectional shape while the third section of the transmission member 66 may be provided with a circular cross-sectional shape. In one embodiment, the shape of the transmission member 66 smoothly varies from the first cross-sectional shape to the second cross-sectional shape along a given section of the transmission member 66.

In one embodiment, the dimension of the distal end 88 is less than that of the third section of the transmission member 66 to increase the flexibility of the distal end 88.

In another embodiment, the dimension of the distal end 88 is greater than that of the third section of the waveguide 66 to flush the blood out of the catheter in which the distal end 88 of the transmission member 66 is inserted as the distal end 88 is moved toward the occlusion.

In a further embodiment, the dimension of the distal end 88 is greater than that of the third section of the transmission member 66 to maximize the opening size in the occlusion while maintaining great flexibility at the distal end 88.

In one embodiment the transmission member can be comprised of a plurality of individual wires. In another embodiment the transmission member can be of generally tubular shape.

In one embodiment, the transmission member such as waveguide 66 is adapted to be used with traditional PTA devices. In one embodiment, the transmission member has a diameter that is less than about 0.125 inches, and preferably less than about 0.035 inches. In one embodiment, the aspect ratio (defined as: length/diameter) of the transmission member is chosen to be greater than 100, and preferably greater than 1000. In one embodiment, the transmission member has a length comprised between about 60 in and about 120 in. In another embodiment, the transmission member has a length comprised between about 36 in and about 200 in.

In one embodiment, at least the distal section of the transmission member is flexible so as to be bent or curved substantially easily during the intended application. For example, the aortic arch can have a radius of curvature of about 1 in. Therefore, the flexible transmission member may be bent to present a radius of curvature of about 1 in or less.

In one embodiment, the transmission member may have a proprietary interface at its proximal end so that only the latter can be connected to the energy source. This can take the form of added features at the proximal end of the transmission member. Also, a proprietary acoustic signature of the transmission member can be detected using a pulse-echo technique at the beginning of the procedure. An electronic chip that can only be recognized by the proprietary connector may also be used.

In one embodiment, the transmission member may be made of nitinol, stainless steel, titanium alloy, fused quartz or the like. These materials provide an adequate amount of acoustic wave transmission, stiffness and torque transmissibility. However, a fluid or a gas transmission member may also be used.

Figure 14:
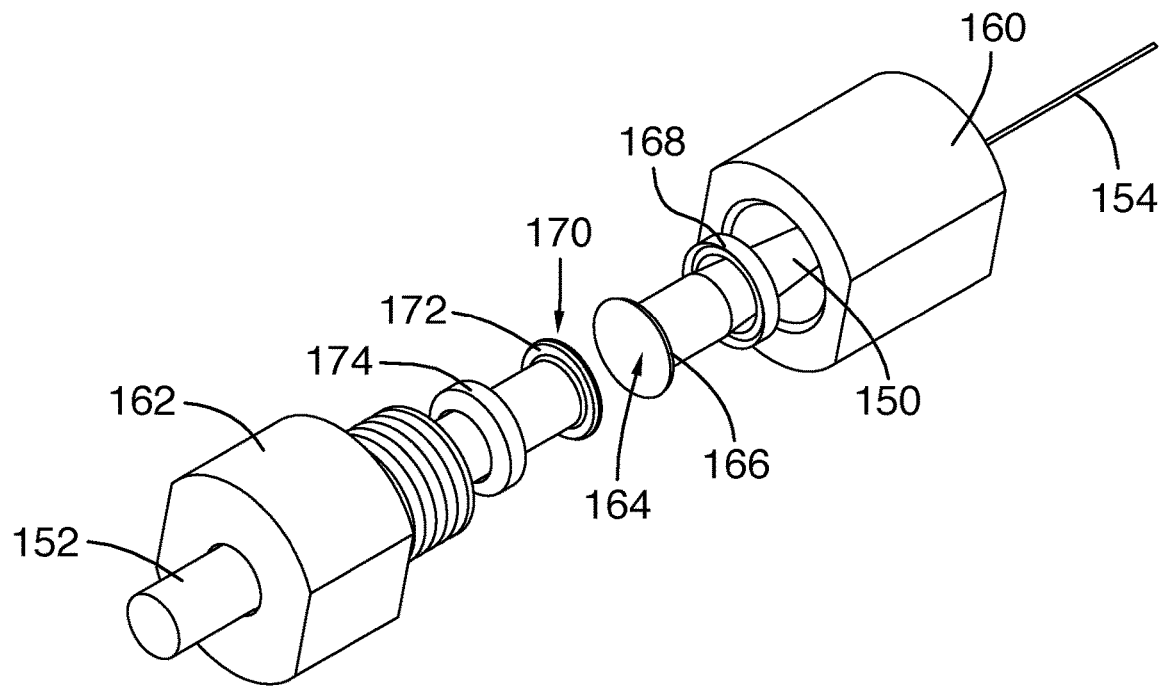
FIG. 14 is a perspective view of a connection system for removably connecting together a taper and a dispersive waveguide, the connection system being in an open position, in accordance with an embodiment.
Figure 15:
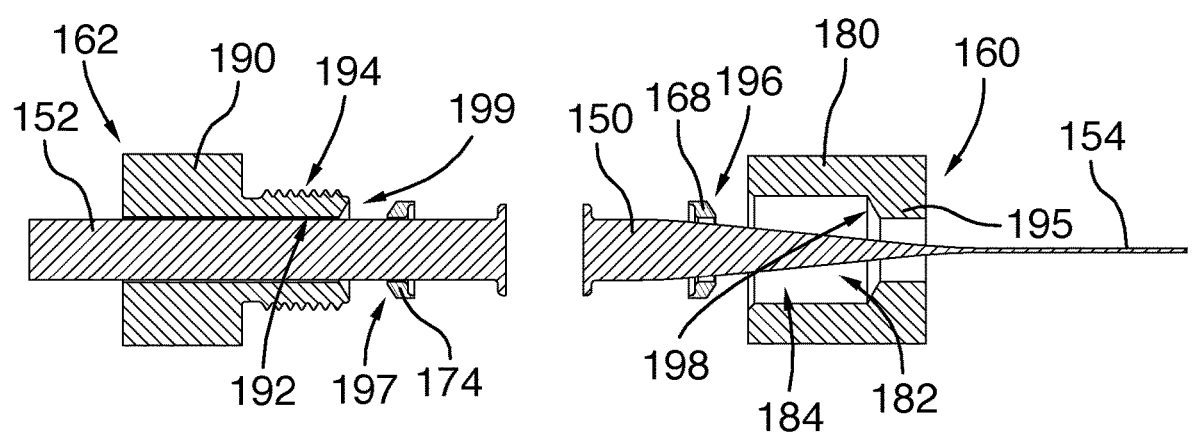
FIG. 15 is a cross-sectional side view of the of the connection system of FIG. 14, when in the open position.
Figure 16:
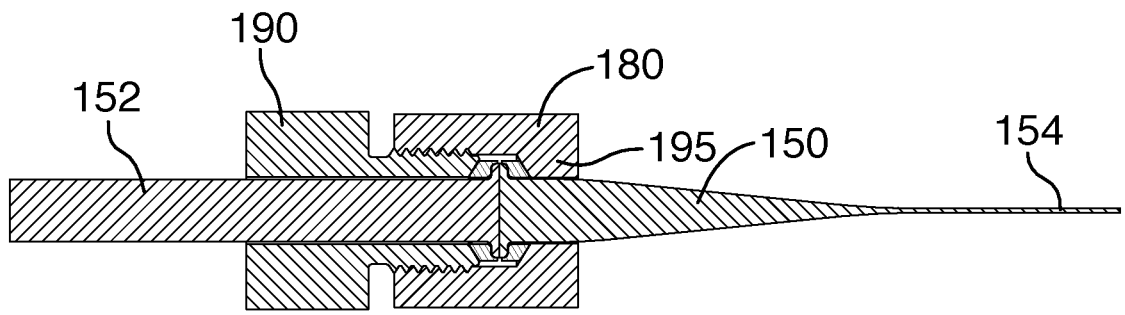
FIG. 16 is a cross-sectional side view of the of the connection system of FIG. 14, when in a closed position.

As described above, two components or elements of the system 50 may be removably secured together. FIGS. 14-16 illustrate such as a configuration in which a taper 150 is removably secured to a dispersive waveguide 152. It should be understood that the waveguide 152 may also be non-dispersive. FIGS. 14-16 further illustrate a transmission member 154 that is integral with the taper 150. Alternatively, the taper 150 and the transmission member 154 may be welded together. A female connector 160 and a male connector 162 form a connection device that is used for removably connecting together the taper 150 and the dispersive waveguide 152. It should be understood that the connection device illustrated at FIGS. 14-16 may be used for connecting together any king of mechanical waveguides having a flange at the connecting end such as tapers, waveguides having a constant diameter, and/or the like.

The proximal end 164 of the taper 150 is provided with a flange 166 which extends radially and outwardly from the taper 150 along the circumference of the proximal end 164. A bushing 168 is inserted around the taper 150 and positioned at a position that is adjacent to the proximal end 164 thereof. It should be understood that the taper 150 is received in the bushing 168 and the bushing 168 may translate along the taper 150. Similarly, the distal end 170 of the dispersive waveguide 152 is provided with a flange 172 which extends radially and outwardly from the dispersive waveguide 152 along the circumference of the distal end 170. A bushing 174 is inserted around the dispersive waveguide 152 and positioned at a position that is adjacent to the distal end 170 thereof. It should be understood that the taper is received in the bushing 168 and may translate along the taper 150. The bushings 168 and 174 are used for alignment purposes and they may be made of a plastic or a metallic material in order to reduce energy leakage.

While in the illustrated embodiment, the flanges 166 and 172 extend along the whole circumference of the proximal end 164 and the distal end 170, respectively, it should be understood that at least one of the two flanges 166 and 172 may extend only along a portion of the circumference of its respective end 164, 170. It should be understood that the diameter of the flanges 166 and 172 may vary as long as it is greater than the diameter of the proximal end 164 of the taper 150 and the diameter of the distal end 170 of the dispersive waveguide 152, respectively. While in the illustrated embodiment, the flanges 166 and 172 have substantially the same diameter, other configurations may be possible.

The female connector 160 comprises a tubular body 180 provided with an aperture 182 which extends between proximal and distal ends thereof and in which the taper 150 and optionally the transmission member 154 are inserted. The cross-sectional dimension of the aperture 182 is greater than that of the assembly formed by the taper 150 and the transmission member 154 so that the taper 150 may slide within the aperture 182 and the female connector 160 may rotate about the taper 150. The section 184 of the internal wall of the body 180 that is adjacent to the proximal end of the female connector 160 is threaded.

The male connector 162 comprises a tubular body 190 provided with an aperture 192 which extends between proximal and distal ends thereof and in which the dispersive waveguide 152 is inserted. The cross-sectional dimension of the aperture 192 is greater than that of the dispersive waveguide 152 so that the dispersive waveguide 152 may slide within the aperture 192 and the male connector 162 may rotate about the dispersive waveguide 152. The section 194 of the internal wall of the body 190 that is adjacent to the distal end of the male connector 162 is threaded and its thread matches that of the section 184 of the female connector so that the threaded section 194 of the male connector 162 may be screwed into the threaded section 184 of the female connector 160.

In order to secure the female and male connectors 160 and 162 together, the taper 150 is inserted into the female connector 160 until the distal beveled end 196 of the bushing 168 abuts a beveled surface 198 of a protrusion that extends from the internal wall of the body 180, as illustrated FIG. 16. The distal end 170 of the dispersive waveguide 152 is inserted into the female connector until it abuts against the proximal end 164 of the taper 150. Then the threaded section 194 is screwed into the female connector. By screwing the male connector 162 into the female connectors 160, the proximal beveled end of the bushing 174 abuts a beveled surface of the internal wall of the body 190.

The beveled surface of the bushing 168 and the corresponding beveled surface of the internal wall of the body 180 cooperate together to center the taper 150 within the aperture 182 of the female connector 160 so that the female connector 160 is not in physical contact with the taper 150 or the transmission member 154 to prevent or at least reduce energy leakage. Similarly, the beveled surface 197 of the bushing 174 and the corresponding beveled surface 199 of the distal end of the body 190 cooperate together to center the dispersive waveguide 152 within the aperture 192 of the male connector 162 so that the male connector 162 is not in physical contact with the dispersive waveguide 152 to prevent or at least reduce energy leakage.

In one embodiment, an impedance matching material may be inserted between the dispersive waveguide 152 and the taper 150. Furthermore, a glycerin film may be added between the dispersive waveguide 152 and the taper 150 to ensure an optimal coupling between the two and to ensure that the longitudinal mechanical wave may be transmitted.

In another example, a film of ultrasonic gel is inserted between the dispersive waveguide 152 and the taper 150.

It should be understood that the connectors 160 and 162 may be made of any adequate material such as stainless steel, titanium alloy, plastic, or the like.

In one embodiment, the flanges 166 and 172 have a thickness that is less than the central wavelength of the mechanical pulse to minimize diffraction of the mechanical pulse in the flanges 166 and 172.

In one embodiment, the flanges 166 and 172 may be omitted and replaced by notches provided in the taper 150 and the dispersive waveguide 152. In this case, the holding mechanism may comprise a grip. With respect to the configuration comprising flanges, the notches allow not increasing the overall diameter of the dispersive waveguide 152 and that of the taper 150.

While in the illustrated embodiment, threaded sections are used to removably secure the two connectors 160 and 162 together, it should be understood that any adequate securing means adapted to removably secure the two connectors together may be used.

Figure 17:
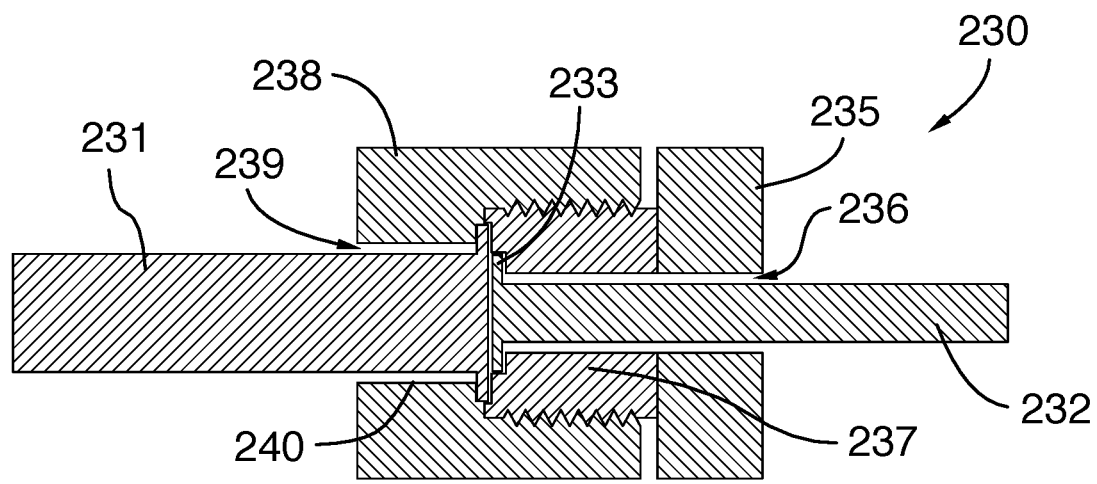
FIG. 17 illustrates a connection system for removably connecting a transmission member and a dispersive waveguide, in accordance with an embodiment.

FIG. 17 illustrates an exemplary configuration of a connection device 230 for removably connecting a first mechanical waveguide 231 such as a dispersive waveguide to a second mechanical waveguide 232 such as transmission member. In this embodiment, the proximal end of the transmission member 232 is provided with a flange 233 and the distal end of the dispersive waveguide 231 is also provided with a flange 234.

The connection device 230 comprises a male connector 235 defining an aperture 236 for receiving the first waveguide 232 therein. The first aperture 236 comprises a first section for receiving the flange 233 of the first mechanical waveguide 232 and a second section. The internal face of the male connector 235 comprises a protrusion 237 defining the second section of the aperture 236. The protrusion 237 comprises an abutment face for abutment against the flange 233 of the mechanical waveguide 232, The dimensions of the second section of the aperture 236 are greater than the dimensions of the mechanical waveguide 232 so that the protrusion 237 is not in physical contact with the lateral face of the mechanical waveguide 232 when the waveguide 232 is inserted into the male connector 235.

The connection device 230 further comprises a female connector 238 which defines an aperture 239 for receiving the mechanical waveguide 231 therein. The aperture 239 comprising a first section for receiving therein the flange 234 of the mechanical waveguide 231 and a portion of the male connector 235, and a second section. The internal face of the female connector 238 comprises a protrusion 240 which defines the second section of the aperture 239. The protrusion 240 comprises an abutment face for abutment against the flange 234 of the mechanical waveguide 231. The dimensions of the second section of the aperture 239 are greater than the dimensions of the mechanical waveguide 231 so that the protrusion 240 is not in physical contact with the mechanical waveguide 231 when the mechanical waveguide 231 is inserted into the female connector 238.

In one embodiment, the apertures 236 and 239 are cylindrical. In this case, the second section of the aperture 236 has a diameter that is greater than that of the mechanical waveguide 232 and that is less than that of the flange of the mechanical waveguide 232. The second section of the aperture 239 has a diameter that is greater than that of the mechanical waveguide 231 and that is less than that of the flange of the second mechanical waveguide.

In one embodiment, the portion of the male connector 235 that is insertable into the female connector 238 comprises a first thread extending on its external surface. The internal surface of the female connector 238 comprises a second thread within the first section of the aperture 239, and the second thread matches the first thread so that the male and female connectors 235 and 238 be threadingly securable together.

In one embodiment, the flange 233 extends around a whole circumference of the mechanical waveguide 232 and the flange 234 extends around a whole circumference of the mechanical waveguide 231.

It should be understood that the connection device 230 may be used for connecting any kind of waveguides provided with a flange. For example, the connection device 230 may be used for connecting together a taper and a cylindrical waveguide.

Once secured together, the male and female connectors are only in physical contact with the flange of the waveguides. Such a configuration allows reducing the surface of contact between the connectors and the dispersive waveguide and the transmission member so as to reduce energy leakage.

In another embodiment, the proximal end of the transmission member may be threaded and the distal end of the dispersive waveguide is provided with a threaded recess in which the transmission member is screwed in order to removably secure the transmission member and the dispersive waveguide together. It should be understood that such a connection may be used for removably securing a taper to a dispersive waveguide, a transmission member to a taper, etc.

Figure 18:
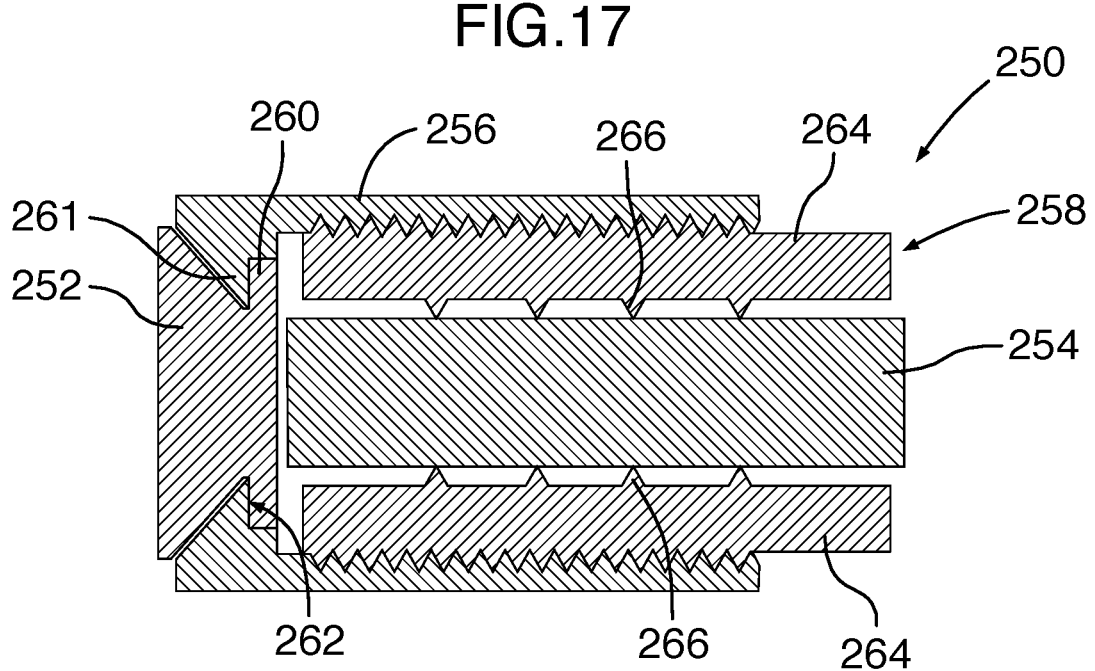
FIG. 18 illustrates a connection system for removably connecting a transmission member and a taper, in accordance with an embodiment.

FIG. 18 illustrates a further example for a connector 250 between a taper 252 and a transmission waveguide 254. The connector assembly comprises a female connector 256 having a tubular shape and being movably mounted on the taper, and a male connector 258 mounted on the transmission member. The distal end of the taper is provided with a flange 260 that radially and outwardly extends around the circumference thereof.

The female connector 256 comprises a tubular body having an internal threaded face and a protrusion 261 having an abutment face 262. The male connector 258 comprises two hemi-tubular bodies 264 that are clamped about the transmission member 254. Each hemi-tubular body 264 is provided with teeth 266, e.g. sharp or pointed protrusions, extending from its internal face, and a threaded outer surface threadingly engageable with the internal threaded surface of the female connector 256. The two hemi-tubular bodies 264 may be clamped about the transmission member 254 using any adequate clamping means. In this case, the teeth 266 create notches in the transmission member 254 and the two clamped hemi-tubular bodies 254 are fixedly secured together and fixedly secured to the transmission member 254 to form a threaded bolt. Once the hemi-tubular bodies 264 have been clamped about the transmission member 254, the threaded bolt is screwed into the female connector 256. While the threaded bolt is screwed into the female connector, the abutment face 262 of the female connector 256 abuts against the flange 260 of the taper 252 and the distal end of the taper 252 abuts against the proximal end of the transmission member 254.

In another embodiment, the two hemi-tubular bodies 264 may not be clamped together. In this case, the two hemi-tubular bodies 264 are pushed against the waveguide 254 and the assembly formed of the two hemi-tubular bodies 264 and the waveguide 254 is screwed into the female connector 256

In one embodiment, the use of the teeth 266 for securing the transmission member 254 to the male connector 258 allows minimizing the surface area of the transmission member 254 that is in physical contact with the male connector 258, thereby minimizing the propagation losses for mechanical pulses propagating in the transmission member 254.

In one embodiment, the external surface of the transmission member 254 is provided with grooves that are each shaped and sized for receiving a respective tooth 266 therein. For example, the shape and dimensions of the grooves may substantially correspond to those of the teeth so each tooth may be snuggingly inserted into its respective groove. In this case, the insertion of the teeth 266 in their respective grooves allows preventing any translation of the transmission member 254 along the longitudinal axis thereof relative to the male connector 258.

In one embodiment, the grooves may result from the clamping of the two hemi-tubular bodies 264 which pushes the teeth 266 into the transmission member 254, thereby creating the groves. In this case, the teeth 266 may be made of a material having a greater hardness than that of the material of which the transmission member 254 is made.

In another embodiment, the grooves may be made prior to the securing of the male connector 258 thereon.

While in the illustrated embodiment, the teeth of the two hemi-tubular bodies 264 are aligned together, i.e. each tooth of one of the two hemi-tubular bodies 264 is aligned with a respective tooth of the other one of the two hemi-tubular bodies 264, it should be understood that the teeth of the two hemi-tubular bodies 264 are misaligned.

It should also be understood that the number, position, and orientation of the teeth 26 on each one of the two hemi-tubular bodies 264 may vary. For example, the distance between two following teeth may vary along the internal face of the hemi-tubular bodies 264.

It should be understood that the teeth 266 may be provided with any adequate shape. In one embodiment, the teeth 266 may be sharp or pointed. For example, the teeth may have a pyramidal shape, a conical shape, or the like. In another example, the teeth may be rounded.

While in the illustrated embodiment the male connector 258 comprises two hemi-tubular bodies 264, it should be understood that the male connector 258 may comprise a single hemi-tubular body 264. In this case, securing means are used to fixedly secure the hemi-tubular body 264 to the transmission member 254. For example, a cable tie may be used.

In one embodiment, the teeth 266 are made of the same material than that of which the transmission member 254 is made. In another embodiment, the teeth 266 and the transmission member 254 are made of different materials. For example, the teeth 266 may be made of a material having a greater hardness than that of the material of which the transmission member 254 is made.

While in the illustrated embodiment, the teeth 266 project from the hemi-tubular bodies 264, the person skilled in the art would understand that the teeth 266 may be omitted and replaced by teeth that project radially and outwardly from the lateral surface of the transmission member 254. In this case, the teeth projecting from the transmission member 254 create notches in the internal surface of the two hemi-tubular bodies 264 when the two hemi-tubular bodies 264 are secured or clamped together, thereby securing the two hemi-tubular bodies 264 to the transmission member 254.

In one embodiment, the bandwidth of the energy source used in the present system, which is expressed as a percentage of the center frequency $f_c$, is greater than about 10%, and preferably between about 40% and about 120%. The center/main frequency $f_c$ of the broadband energy source may vary between about 20 kHz and about 10 MHz and is preferably between about 0.1 MHz and about 1 MHz.

The broadband source power and the level of control over the output of the broadband source can be characterized by the pulse duration, repetition rate, pressure amplitude, polarity and waveform type. In one embodiment, the mechanical pulse duration at the distal end of the transmission member is usually of the order of $1/f_c$. For example, an energy source having a center frequency of 500 kHz will generate a mechanical pulse having duration of about 2 μs, when a bandwidth of 100% (i.e. a Q factor of 1) is considered. In one embodiment, the mechanical pulse duration can be varied by changing the center frequency or the bandwidth (i.e. Q factor) of the energy source; the pulse duration is preferably less than about 1 µs.

The pulse repetition rate is associated with the number of pulses that can be transmitted during a certain amount of time. In one embodiment, the repetition rate can be varied between about 0.1 Hz and about 1000 Hz and is preferably between about 10 Hz and about 200 Hz.

In one embodiment, the output pressure amplitude of the mechanical pulse generated at the output of the transmission member is greater than about 10 MPa in both compression and tension. In one embodiment, the output pressure amplitude is comprised between about 10 MPa and about 1000 MPa in compression and between about 10 MPa and about 500 MPa in tension, when measured at the distal end of the transmission member in a fluid medium.

The amplitude of the generated mechanical pulse may be modified using different methods. For example, increasing or decreasing the driving voltage of at least one of the transducers would cause the mechanical pulse amplitude to vary accordingly. In another example, clipping the electric signals amplitude anywhere between no clipping (original signal) and 100% clipping, where only the sign (polarity) of the driving signal is preserved, would cause the mechanical pulse amplitude to increase accordingly, albeit with an increase of the amplitude of the parasitic mechanical waves preceding and following the mechanical pulse.

The polarity is defined as the ability to reverse the sign of the pressure amplitude profile of the output mechanical pulse. The control over the waveform type can be defined as the ability to generate more than one pulse shape. For example, it may be useful to lengthen only the tensile part of the waveform or to add oscillations to treat a specific occlusion type.

The polarity of the generated mechanical pulse may be reversed without the need of re-calibrating the system for that particular mechanical pulse. Indeed, for a linear system (as opposed to a non-linear system), the polarity of the generated pulse may be reversed by negating, i.e. multiply by −1, the transducer driving signals.

The shape or temporal signature of the generated mechanical pulse may also be controlled electronically. In one embodiment, the system would keep in its memory sets of driving signals for the transducers, each set corresponding to a unique pulse shape. In another embodiment, the shape of the mechanical pulse may be modified by making algebraic combination(s) of the electrical driving signals with themselves such that the same algebraic combination(s) would then be impacted on the pulse itself. The workflow would be as follows. A first mechanical pulse would be measured at the distal end of the transmission member. Next, modified version(s) of the acquired first mechanical pulse would be digitally constructed and serve as building blocks and summed to create the pulse of altered shape. The modified versions are created by delaying and/or multiplying (by a given factor) the first mechanical pulse. Finally, equivalent version(s) would be made from the electrical driving signal(s) and their summation would become the new driving signals. These composed driving signals would then generate the pulse of altered shape at the distal end of the transmission member.

In order to achieve at least some of the above-listed characteristics, the system 50 may be used. However, the person skilled in the art will understand that other configurations are possible.

In one embodiment, the system 50 illustrated in FIG. 3 allows achieving an amplification factor greater than 100×. The amplification factor is defined as the maximum output pressure ratio between the system 50 and a single electromechanical broadband transducer. These pressures are usually measured in water, at the same distance, on the same surface area and using the same output waveform for both configurations. In one embodiment, an amplification factor of this order of magnitude may provide the ability to reduce the input electrical power and/or the electromechanical emitting surface area. Therefore, the cost of goods and/or the apparatus overall footprint could be downsized accordingly.

In one embodiment, the sources 54-58 are electromechanical broadband sources. By doing so, the device has the capability of working in a pulse-echo mode to image/characterize biological tissues located just in front of the distal end of the transmission waveguide. Moreover, an electromechanical broadband source may provide an adequate level of control desired to cross vascular occlusion efficiently and safely.

Figure 5:
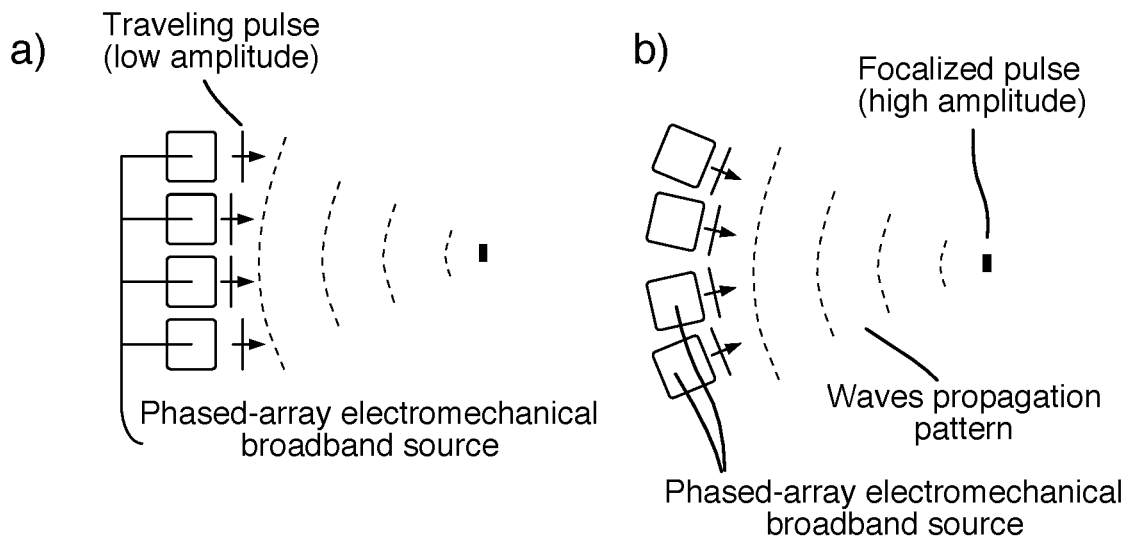
FIG. 5 illustrates a phased-array electromechanical broadband source, in accordance with an embodiment.
Figure 6:
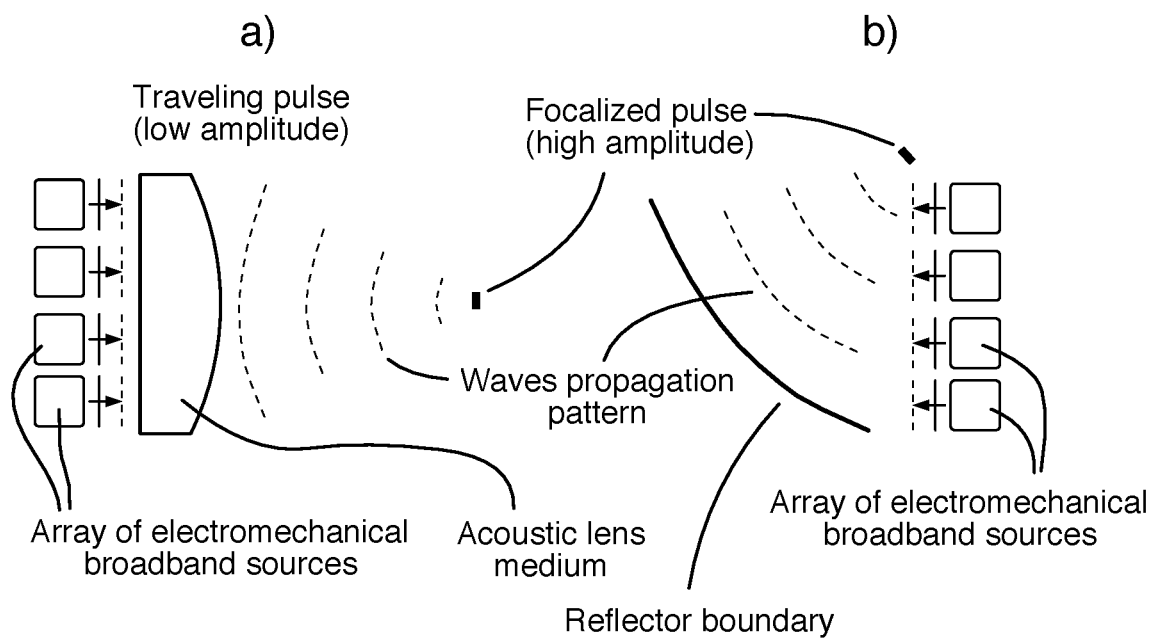
FIG. 6a illustrates an array of electromechanical broadband sources cooperating with an acoustic lens, in accordance with an embodiment.
FIG. 6b illustrates an array of electromechanical broadband sources cooperating with a reflector, in accordance with an embodiment.

The following presents a specific exemplary implementation for the system 50 illustrated in FIG. 3 in which the concentrator 81 illustrated in FIGS. 4-6 are used. Nine broadband piezoelectric transducers are used, comprising four 1 inch diameter transducers and five 2 inches diameter transducers. These transducers have a bandwidth of 80% (corresponding to a Q factor of about 1.25). Eight transducers, i.e. four 1 inch diameter transducers and four 2 inches diameter transducers, are distributed symmetrically on the propagation face of the concentrator 81, and a single 2 inches diameter transducer is positioned on the reflection truncated face of the concentrator 81. The concentrator 81 has the following dimensions: a diameter of about 6.25 inches and a thickness of about 2 inches. The concentrator 81 is made of a titanium alloy. Also, the focal zone is located at the same plane where the eight transducers are positioned. The concentrator 81 produces an amplification factor of about 4× when compared to a single piezoelectric transducer having the same size as the useful focal zone. The temporal concentrator 62 has a cylindrical shape and is made of the same titanium alloys as the concentrator 81. Furthermore, the temporal concentrator 62 has the following dimensions: a diameter of about 0.25 in and a length of about 50 feet. In order to limit its footprint, the spatial concentrator is coiled to a radius of curvature of about 14 in. The geometry, dimension and medium of the temporal concentrator are selected accordingly to the wavelength of operation in order to maximize the amplification factor. Taking advantage of the dispersive properties of the temporal concentrator 62, an amplification factor of at least 15× is achieved between the input and the output end of the temporal concentrator 62. The proximal end of the temporal concentrator 62 is welded at the focal zone of the spatial concentrator 81 to allow an optimal wave transmission between the two parts. At the distal end of the dispersive waveguide 62, a second stage spatial concentrator is added. This spatial concentrator takes the form of a tapering waveguide 64 having a proximal end diameter of about 0.25 inches and a distal end diameter of about 0.014 inches. The tapering waveguide 64 is about 3 inches long and is made of the same titanium alloy.

The amplification factor associated with the tapering waveguide 64 is about 2×. The proximal end of the concentrator 64 can be welded to the distal end of the dispersive waveguide 62 or removably connected using the above-described connector. The proximal end 86 of the elongated and flexible transmission waveguide 66 is secured to the distal end of the concentrator 64. Similar securing methods may be used, e.g., welding, using a removable connector, or the like. The overall amplification factor of the device is about 120× after the concentrator 64. The transmission member 66 is a wire made of suitable alloy like Ti-11.5Mo-6Zr-4.5Sn (Beta III titanium) and having a diameter comprised between about 0.040 inches and about 0.004 inches and a length of about 120 inches. A person skilled in the art will understand that different geometry, configuration, component, energy source, wavelength of operation, propagating medium, and/or the like can be used to achieve the above-described system/method for crossing occlusions using a broadband energy source that generates and transmits short, high pressure and customizable pulses up to the distal end of a transmission member.

In one embodiment, the present method and system allow crossing vascular occlusions using a broadband source with a transmission member. This method and system are most likely to be safer and more effective compared to traditional PTA techniques. A broadband energy source that is external to the body of the patient is used to generate mechanical waves that propagate across an elongated and flexible transmission member up to the site of the vascular occlusion. Pulsed and controlled mechanical wave emission at the distal end of the transmission member may crack, cleave, erode, tunnel and/or break parts of the occlusion. By doing so, the occlusion is easier to cross using the present system and method than traditional PTA devices.

In one embodiment, the use of a broadband source to cross vascular occlusions provides the ability to tailor the treatment according to the lesion specific composition and characteristics. Treatment customization can be achieved by varying the pulse duration, repetition rate, pressure amplitude, polarity, and/or waveform type. Adjustments of the output mechanical pulse can be made once at the beginning or live during the procedure.

In one embodiment, because it is external to the patient body, the energy source may be used multiple times without risk of contamination. Moreover, because it is situated outside of the patient body, the energy source is not constrained in power, size or geometry.

In one embodiment, the elongated and flexible transmission member can be used with or without traditional PTA devices such as guidewire, micro-catheter, catheter, over-the-wire balloon, or the like to facilitate accessing, guiding and crossing of the vascular occlusion. By doing so, the present system may be inserted into the workflow of standard PTA procedures.

While they are described in a medical context, i.e. for crossing vascular occlusions, it should be understood that the above methods and systems may be used for other medical or non-medical applications. For example, the methods and systems may be used to fragment kidney stones, enhance and improve the delivery of chemicals and drugs, increase the mechanical compliance of vascular lesions prior to the use of balloon, and/or unclog and recanalize shunt catheter, catheter, micro-catheter, endoscope and/or other medical tubular instruments. The above-described method and system may also be used to soften calcified cardiac valves, free pacemaker leads and other medical device embedded in calcified and/or fibrotic tissue. The methods and systems may also have applications in other medical fields. For example, they may be used for dental and orthopedic drilling, anchor (bolt, sealant, crown, etc.) removing, and/or surface cleaning.

The above-described methods and system of generating mechanical pulses may have applications in fields other than the medical field. For example, they may be used for machining and shaping materials such as brittle materials, for solution mixing and homogenization, unclogging pipes, hole drilling, and/or the like.

In one embodiment, the above-described system 20 can be used to image or characterize an object, tissue or a surrounding area located in front of the distal end of the transmission member. To do so, a broadband source that can work both as an emitter and as a receiver may be used. In order to image an object, a mechanical pulse is first delivered at the distal end of the transmission member. Following transmission into the surrounding medium, parts of the mechanical pulse are reflected back into the transmission member. These echoes travel back the system 20 and are converted into an electrical signal by the broadband source. Post-processing analysis can be performed to treat this signal and convert it into useful information. To perform imaging, the broadband mechanical source of system 20 can be the same as the one use for emission or can be a different one. For example, one can want to use a broadband mechanical source at a higher center frequency (>10 MHz) so to increase the spatial resolution of the imaging.

The embodiments of the invention described above are intended to be exemplary only. The scope of the invention is therefore intended to be limited solely by the scope of the appended claims.

The invention claimed is:

1. A method for generating a mechanical wave for treating a lesion in a blood vessel, comprising:
   generating, using a wave generator, at least one high amplitude broadband mechanical pulse;
   coupling the at least one high amplitude broadband mechanical pulse into a proximal end of a non-dispersive transmission member, at least a section of the non-dispersive transmission member being inserted into the blood vessel, a distal end of the non-dispersive transmission member being positioned adjacent to the lesion in the blood vessel;
   propagating the at least one high amplitude broadband mechanical pulse into the non-dispersive transmission member from the proximal end to the distal end thereof; and
   transmitting the at least one high amplitude mechanical pulse at the distal end of the non-dispersive transmission member to thereby treat the lesion.

2. The method of claim 1, wherein the at least one high amplitude broadband mechanical pulse each have a center frequency $f_c$ comprised between about 20 kHz and about 10 MHz and a duration of about $1/f_c$.

3. The method of claim 1, wherein an amplitude of the at least one high amplitude broadband mechanical pulse when reaching the distal end of the non-dispersive transmission member is comprised between about 10 MPa and about 1000 MPa.

4. The method of claim 1, wherein said generating comprises generating a plurality of broadband mechanical waves having a first amplitude and combining the plurality of broadband mechanical waves, thereby obtaining the at least one high amplitude broadband mechanical pulse each having a second amplitude greater than the first amplitude.

5. The method of claim 4, wherein said combining comprises focusing the plurality of broadband mechanical waves on a focus zone.

6. The method of claim 5, wherein said focusing comprising reflecting the plurality of broadband mechanical waves on a parabolic surface.

7. The method of claim 4, wherein said combining comprising propagating the plurality of broadband mechanical waves into a temporal concentrator.

8. The method of claim 4, wherein said combining comprises propagating the plurality of broadband mechanical waves in a taper.

9. The method of claim 4, wherein said combining comprises propagating the plurality of broadband mechanical waves in a reverberating cavity.

10. The method of claim 4, wherein said combining comprises propagating the plurality of broadband mechanical waves in a dispersive medium.

11. The method of claim 1, wherein the non-dispersive transmission member has an aspect ratio equal to or greater than 1000.

12. A system for generating a mechanical wave for treating a lesion in a blood vessel, comprising:
   a pulse generator for generating at least one high amplitude broadband; and
   a non-dispersive transmission member extending between a proximal end and a distal end, the proximal end being coupled to the pulse generator for receiving the at least one high amplitude broadband mechanical pulse therefrom, at least a section of the non-dispersive transmission member being sized and shaped to be insertable into the blood vessel, the distal end of the non-dispersive transmission member being positionable adjacent to the lesion, the non-dispersive transmission member for propagating the at least one high amplitude broadband mechanical pulse from the proximal end to the distal end and transmitting the at least one high amplitude broadband mechanical pulse at the distal end to thereby treat the lesion.

13. The system of claim 12, wherein the at least one high amplitude broadband mechanical pulse each have a center frequency $f_c$ comprised between about 20 kHz and about 10 MHz and a duration of about $1/f_c$.

14. The system of claim 12, wherein an amplitude of the at least one high amplitude broadband mechanical pulse when reaching the distal end of the non-dispersive transmission member is comprised between about 10 MPa and about 1000 MPa.

15. The system of claim 12, wherein the pulse generator comprises:
   a plurality of broadband sources each for emitting a respective broadband mechanical wave having a first amplitude; and
   a wave concentrator for combining the broadband mechanical waves in order to obtain the at least one high amplitude broadband mechanical pulse having a second amplitude greater than the first amplitude.

16. The system of claim 15, wherein the wave concentrator is a spatial concentrator.

17. The system of claim 15, wherein the wave concentrator is a temporal concentrator.

18. The system of claim 15, wherein the wave concentrator is adapted to focus the mechanical waves on a focus zone adjacent to the proximal end of the non-dispersive transmission member.

19. The system of claim 18, wherein the wave concentrator comprises a parabolic reflecting surface for reflecting at least some of the plurality of broadband mechanical waves generated by the plurality of broadband sources towards the focus zone.

20. The system of claim 15, wherein the wave concentrator is a taper.

21. The system of claim 15, wherein the wave concentrator comprises a spatial concentration stage and a temporal concentration stage.

22. The system of claim 15, wherein the wave concentrator comprises a reverberating cavity.

23. The system of claim 15, wherein the wave concentrator comprises a dispersive medium.

24. The system of claim 12, wherein the non-dispersive transmission member has an aspect ratio equal to or greater than 1000.

* * * * *